United States Patent
Maddon et al.

(10) Patent No.: US 6,570,000 B1
(45) Date of Patent: *May 27, 2003

(54) DNA ENCODING THE T CELL SURFACE PROTEIN CD4 AND USE OF FRAGMENTS OF CD4 IN THE TREATMENT OF AIDS

(75) Inventors: Paul J. Maddon, New York, NY (US); Dan R. Littman, San Francisco, CA (US); Leonard Chess, Scarsdale, NY (US); Richard Axel, New York, NY (US); Robin Weiss, London (GB)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/470,998

(22) Filed: Jun. 6, 1995

Related U.S. Application Data

(63) Continuation of application No. 08/462,138, filed on Jun. 5, 1995, now Pat. No. 5,871,913, which is a continuation of application No. 08/010,481, filed on Jan. 28, 1993, now abandoned, which is a continuation of application No. 07/713,564, filed on Jun. 11, 1991, now abandoned, which is a continuation of application No. 06/898,587, filed on Aug. 21, 1986, now abandoned.

(51) Int. Cl.[7] .................. C07H 21/04; C07H 21/02; C12P 21/06; C12N 1/21
(52) U.S. Cl. .................. 536/23.1; 435/69.1; 435/252.3; 435/320.1; 435/325; 435/255.1; 435/348; 530/395
(58) Field of Search .................. 435/6, 5, 91.2, 435/69.1, 325, 320.1, 252.3, 255, 1, 348; 536/23.1, 24.3–24.33; 530/350, 395, 827; 930/10

(56) References Cited

U.S. PATENT DOCUMENTS

| | | | |
|---|---|---|---|
| 4,520,113 A | 5/1985 | Gallo et al. | |
| 4,621,054 A | 11/1986 | Suzuki et al. | |

(List continued on next page.)

FOREIGN PATENT DOCUMENTS

| | | |
|---|---|---|
| WO | 8801304 | 2/1988 |
| WO | 8901940 | 9/1989 |
| WO | 8908143 | 9/1989 |

OTHER PUBLICATIONS

Barr, P.J. et al., (1989) Yeast Genetic Engineering, Chapter 17 (Exhibit 4).

(List continued on next page.)

*Primary Examiner*—S. Zitomer
(74) *Attorney, Agent, or Firm*—John P. White; Cooper & Dunham LLP

(57) ABSTRACT

A single-stranded nucleic acid molecule which encodes an amino acid sequence comprising at least a portion of a T4 glycoprotein is provided. Additionally, amino acid sequences which comprise at least a portion of a T4 glycoprotein and are useful as a prophylaxis for treating a subject with acquired immune deficiency syndrome are provided. These amino acid sequences, which are capable of specifically forming a complex with a human immunodeficiency virus envelope glycoprotein and which are soluble in an aqueous solution may be administered to a subject infected with a human immunodeficiency virus so as to block the human immunodeficiency virus from binding to $T4^+$ cells.

Monoclonal antibodies directed to the water-soluble amino acid sequences of the present invention may be used as vaccines for immunizing a subject against acquired immune deficiency syndrome.

10 Claims, 21 Drawing Sheets

U.S. PATENT DOCUMENTS

| | | |
|---|---|---|
| 4,629,783 A | 12/1986 | Cosand |
| 4,663,436 A | 5/1987 | Elder et al. |
| 4,761,371 A | 8/1988 | Bell et al. |
| 4,816,567 A | 3/1989 | Cabilly et al. |
| 5,110,906 A | 5/1992 | Maddon et al. |
| 5,126,433 A | 6/1992 | Maddon et al. |

OTHER PUBLICATIONS

Blue, M., et al., (1985) J. of Immunology, 134:2281–2286.

Carr, S.A., et al., (1989) J. Biol. Chem. 264:21286–21295 (Exhibit 5).

Dalgleish, A.G., et al., (1984) Nature, 312:763–767 (Exhibit 6).

Isobe, M., et al., (1986) Proc. Natl. Acad. Sci. USA, 83:4399–4402.

Klatzman, D., et al., (1984) Nature, 312:767–768 (Exhibit 7).

Littman, D.R., et al., (1985) Chemical Abstracts, 103:175, col. 1, abstract No. 190738.

Littman, D.R., et al., (1985) Cell, 40:237–246 (Exhibit 8).

Littman, D.R., et al., (1985) ICSU Short Reports, 2:233–234 (Exhibit 9).

Maddon, P.J., et al., (1985) Cell, 42:93–104 (Exhibit 10).

Maddon, P.J., et al., (1986) Cell, 47:333–348.

McDougal, J.S., et al., (1986) J. of Immunology, 137:2937–2944.

McDougal, J.S., et al., (1986) Science, 231:382–385.

Murre, C., et al., (1986) Molecular and Cellular Biology, 6:1315–1319 (Exhibit 11).

Possee, R.D., (1986) Virus Research, 5:43–49 (Exhibit 12).

Ratner, L., et al., (1985) Nature, 313:277–284.

Rose, J.K. and Bergmann, J.E. (1982) Cell, 30:753–762.

Springer, T.A. and Strominger, J.L., (1976) Proc. Natl. Acad. Sci. USA, 73(7):2481–2485.

Terhorst, C., et al., (1980) Science, 209:520–521 (Exhibit 13).

Wills, J.W., et al., (1984) J. Cell Bio., 99:2011–2023; and

Wong–Staal, F., et al., (1985) Nature, 317:395–403.

FIGURE 6

```
CAAGCCAGAGCCCTCCATTCTGTGGGCTCAGTCCTACTCTCCTCCTCCTGGCAAGCCACA
                                              -1 +1
         -10
leu val leu gln leu leu ala leu pro ala ala thr gln gly asn lys val val leu gly asp thr val glu leu thr
CTG GTG CTG CAA CTG CTC GCG CTC CCA GCA ACC ACT CAG AAC GGA AAC GTG GTC CTG GGC GAT ACA GTG GAA CTG ACC      108
                                                                        V1
         +20                                    +30
thr ala ser gln lys lys ser ile gln phe his phe lys asn ser phe leu thr lys
ACA GCT TCC CAA AAG AAG AGC ATA CAA TTC CAC TTC AAA AAC TCC TTC TTA ACT AAA                                  198
                                                                                                    •
         +50                                    +60
gly pro ser lys leu asn asp arg ala asp arg ser arg arg ser phe asn gln gly ser phe leu thr lys ile lys asn leu lys ile
GGT CCA AAG CTG AAT GAT CGC GCT GAC AGA AGA AGC TGT GAC CAA GGA AAT CAG GGC TCC TTC TTA ACT AAG AAT CTT AAG ATA   378
                       +80                                    +90                                   +100
glu asp thr tyr ile cys glu val gln lys glu val glu val phe gly leu thr ala asn ser asp thr
GAA GAC TCA GAT ACT TAC ATC TGT GAA GTG CAG AAG GAG GTG GAA GTG TTC GGA TTG ACT GCC AAC TCT GAC ACC       468
                                                                                    •
         +110                                   +120                                   +130                       J1
his leu gln gly gln ser leu thr leu glu ser pro pro gly ser ser val gln cys arg ser pro arg gly lys
CAC CTG CTT CAG GGG CAG AGC CTC ACC CTG GAG TCC CCT GGT AGC AGC GTC CAA TGT AGG AGT CCA AGG GGT AAA       558
                                                                                                    •
         +140                                   +150                                   +160
asn ile glu gln asp gly lys thr leu ser val ser leu thr val gln asp ser gly thr trp thr cys thr val leu gln asn gln lys
AAC ATA GAG CAG GAT GGG AAG ACC CTC TCC GTG TCT CTG ACC GTG CAG GAT AGT GGC ACC TGG ACA TGC ACT GTC TTG CAG AAC CAG AAG 648
         +170                                   +180                                   V2
lys val glu phe lys ile asp ile val val leu ala phe gln lys ala ser ile val tyr lys lys gly glu gln val glu phe
AAG GTG GAG TTC AAA ATA GAC ATC GTG GTG CTA GCT TTC CAG AAG GCC TCC ATC GTA TAT AAG AAA GGG GAA CAG GTG GAG TTC       738
                                                                        V3
         +200                                   +210                                   +220
ser phe pro leu ala phe thr val glu lys leu thr gly ser gly glu leu trp trp gln ala glu arg ala ser ser lys ser trp
TCC TTC CCA CTC GCC TTT ACA GTT GAA AAG CTG ACG GGC AGT GGC GAG CTG TGG TGG CAG GCG GAG AGG GCT TCC TCC AAG TCT TGG       828
```

FIGURE 6 (cont.)

```
+230                                              +240                                              +250
ile thr phe asp leu lys asn lys glu val ser val lys arg val thr gln asp pro lys leu gln met gly lys lys leu pro leu his
ATC ACC TTT GAC CTG AAG AAC AAG GAA GTG TCT GTA AAA CGG GTT ACC CAG GAC CCT AAG CTC CAG ATG GGC AAG AAG CTC CCG CTC CAC   918
                                                                                          V3

+260                                              +270                                              +280
leu thr leu pro gln ala leu pro gln tyr ala gly ser gly asn leu thr leu ala lys thr gly lys leu his gln glu
CTG ACC CTG CCC CAG GCC TTG CCT CAG TAT GCT GGC TCT GGA AAC CTC ACC CTG GCC CTT GAA ACG AAA ACA GGA AAG TTG CAT CAG GAA  1008
                                       J3                            CHO +290                                              +300                                              +310
val asn leu val val met arg ala thr gln leu lys asn leu thr cys glu val trp gly pro thr ser pro lys leu met leu ser
GTG AAC CTG GTG GTG ATG CGA GCC ACT CAG CTC AAA AAT TTG ACC TGT GAG GTG TGG GGA CCC ACC TCC CCT AAG CTG ATG CTG AGC  1098
                      V4                                    CHO +320                                              +330                                              +340
leu lys leu glu asn lys gly ala lys val ser lys arg glu ala gly met trp val leu asn pro val gln pro glu ala gly met trp val leu ser leu
TTG AAA CTG GAG AAC AAG GGA GCA AAG GTC TCG AAG CGG GAA GCG GGG ATG TGG GTG CTG AAC CCT GTG CAG CCT GAG GCG GGG ATG TGG GTG CTG AGT CTG  1188

+350                                              +360                                              +370
leu ser asp ser gly gln val leu leu glu val leu ser asn ile lys val leu pro thr trp ser thr pro val gln pro met ala leu ile val
CTG AGT GAC TCG GGA CAG GTC CTC CTG GAA GTC CTG TCC AAC ATC AAG GTT CTC CCC ACA TGG TCC ACC CCG GTG CAG CCA ATG GCC CTG ATT GTG  1278
                                            J4

+380                                              +390                                              +400
leu gly gly val ala gly leu leu leu phe ile gly leu phe ile phe phe cys val arg cys arg arg his arg arg gln ala glu arg
CTG GGG GTC GCC GGC CTC CTG CTG TTC ATT GGG CTA TTC TTC TGT GTC AGG TGC AGG CGG CAC CGG AGG CAA GCA GAG CGG  1368
                  TM                                                                    CYT +410                                              +420                                              +430
met ser gln ile lys arg leu leu ser glu arg lys thr cys gln cys pro his arg phe gln lys thr cys ser pro ile —
ATG TCT CAG ATC AAG AGA CTC CTC AGT GAG AGG AAG ACC TGC CAG TGC CCT CAC CGG TTT CAG AAG ACA TGT AGC CCC ATT TGA GGCAGGA   1459
                                                                                                    CYT GGCAGGCAGATCCCACTTCAGCTCAGCTCCAGAGTGTCTCGGGGTTCCTCCTCGGGACCCAGGTCTCGGCCTCCTGTTCGTCCTCCTACAATTTG  1578

CCATGTTTCTCCTGGTTAGGCGGGCGTTCACTGGTTGAGTGTCTCTCTAGTTGCAGAGGCCTTAATCACACCGTCCTCACCCCATTTCCTTTCTTCAGCCTAGCCCTTCT  1697

CTCCATTATTTCTCCTCTGACCTCTCCCCACTCTTCATTTGGATCC  1742
```

```
                                370              380              390
T4           S T P V Q P M A L I V L G G V A G L L F I G L G I F F C V R
MHC cl.II β  S T S A Q N K M L S G V G G F V L G L L F L G L G L F I Y F R
                                         ────────────────────────
                                                    TM
```

DNA ENCODING THE T CELL SURFACE PROTEIN CD4 AND USE OF FRAGMENTS OF CD4 IN THE TREATMENT OF AIDS

This application is a continuation of U.S. Ser. No. 08/462,138, filed Jun. 5, 1995, now U.S. Pat. No. 5,871,913, issued Feb. 16, 1999, which is a continuation of Ser. No. 08/010,481, filed Jan. 28, 1993, now abandoned, which is a continuation of Ser. No. 07/713,564, filed Jun. 11, 1991, now abandoned, which is a continuation of Ser. No. 06/898,587, filed Aug. 21, 1986, now abandoned, the contents of which are hereby incorporated by reference into this application.

BACKGROUND OF THE INVENTION

Within this application several publications are referenced by Arabic numerals within parentheses. Full citations for these references may be found at the end of the specification immediately preceding the claims. The disclosures of these publications in their entirety are hereby incorporated by reference into this application in order to more fully describe the state of the art to which this invention pertains.

The different functional classes of T lymphocytes recognize antigen on the surface of distinct populations of target cells. Helper T cells interact largely with macrophages and B cells; cytotoxic T cells interact with a broader range of antigen-bearing target cells. These cellular recognition events are likely to be mediated by the specific association of surface molecules on both effector and target cells. The surface of T cells is characterized by a number of polymorphic, as well as nonpolymorphic, proteins which are restricted for the most part to T lymphocytes. Although most of these molecules are common to all T cells, two classes of surface proteins consistently differ on the different functional classes of T cells, and these proteins have been implicated in T cell-target cell interactions.

One class of surface molecules distinguishes the major functional subsets of T lymphocytes: the surface glycoproteins T4 and T8. Early in thymic development, the glycoproteins T4 and T8 are coexpressed on the surface of thymocytes (1). In the peripheral immune system, the T4 and T8 molecules are expressed on mutually exclusive subsets of T cells and are only rarely expressed on the same cell (2, 3). The T4 molecule is expressed on T cells that interact with targets bearing class II major histocompatibility complex (MHC) molecules, whereas T8-bearing T cells interact with targets expressing class I MHC proteins (4, 5, 6, 7, 8, 9). The T4 population of T lymphocytes contains helper cells, whereas the T8 population contains the majority of cytotoxic and suppressor cells (6, 10). However, rare T4$^+$ T cells can function as cytotoxic or supressor cells (6, 10), suggesting that the expression of T4 or T8 is more stringently associated with MHC class recognition than with effector function. The significance of these molecules in T cell-target cell interactions can be demonstrated by studies with monoclonal antibodies. Antibodies directed against specific epitopes of the T4 molecule (or the murine equivalent L3T4) inhibit antigen-induced T cell proliferation, lymphokine release and helper cell function (7, 8, 11, 12, 13). Similarly, monoclonal antibodies directed against T8 (or the murine equivalent Lyt2) inhibit cytotoxic T cell-mediated killing (14, 15). These observations, along with the fact that T4 and T8 do not reveal significant polymorphism, has led to the hypothesis that T4 and T8 recognize nonpolymorphic regions of class II and class I molecules, respectively.

A second class of proteins thought to differ on different effector T cells are the receptors that recognize antigen in association with polymorphic regions of MHC molecules (16, 17, 18). The interactions of helper T lymphocytes are largely restricted to antigen-bearing target cells expressing class II MHC proteins, whereas cytotoxic and suppressor T cells are restricted to targets bearing class I MHC molecules (4, 5, 6, 7, 8, 9). These specific interactions may be mediated by the T cell receptor (or receptors) that recognize antigen in the context of specific MHC molecules (17, 18). Thus, the T lymphocyte may have two independent receptors capable of recognizing both constant and polymorphic determinants of MHC proteins, and these receptors may be responsible for specific targeting of functionally distinct populations of T cells.

The human acquired immune deficiency syndrome (AIDS) is characterized by a depletion of T4$^+$ lymphocytes. As a consequence, T cell-mediated immunity is impaired in AIDS patients, resulting in the occurrence of severe opportunistic infections and unusual neoplasms. AIDS results from the infection of T lymphocytes with a collection of closely related retroviruses (LAV, HTLV-III, or ARV), now termed human immunodeficiency virus (HIV). The range of infectivity of these agents is restricted to cells expressing the T4 glycoprotein on their surface.

Therefore, the T4 glycoprotein may serve not only as a receptor for molecules on the surface of target cells, but also as a receptor for the AIDS virus. Monoclonal antibodies directed against T4 block AIDS virus infection of T4$^+$ cells in vitro. Furthermore, recent studies have demonstrated that when T4$^+$ T lymphocytes are exposed to AIDS virus, the 110 kd envelope glycoprotein of the virus is associated with the T4 molecule on the most cell. The lymphotropic character of the virus could therefore be explained by the restricted expression of its receptor, T4, in subpopulations of T lymphocytes.

The depletion of T4$^+$ T lymphocytes in AIDS results in the impairment of the cellular immune response. In addition, AIDS is trequently accompanied by central nervous system (CNS) dysfunction, most often the consequence of a subacute encephalitis. AIDS virus RNA and DNA has been identified in affected brains, and virus has been isolated from both brain and cerebrospinal fluid from patients with neurological disorders. These observations suggest that the AIDS virus infects brain cells and is directly responsible for the CNS lesions observed in AIDS patients. Thus, the AIDS virus may be neurotropic as well as lymphotropic. It is therefore important to determine whether T4 is also expressed in the CNS or whether additional brain-specitic surface molecules may serve as a receptor for the AIDS virus.

The elucidation of the specific interactions of T4 and T8 would be facilitated by the isolation of the T4 and T8 genes, the determination of their structure, and the ability to introduce them into different cellular environments. The isolation and sequence of a cDNA encoding the T8 molecule has recently been reported (19, 20, 21). The deduced protein sequence indicates that T8 is a membrane-bound glycoprotein with an N-terminal domain that bears homology to the variable region of immunoglobulin light chains.

SUMMARY OF THE INVENTION

The present invention provides a single-stranded nucleic acid molecule which encodes an amino acid sequence comprising at least a portion of a T4 glycoprotein. Also provided is an amino acid sequence comprising at least a portion of a T4 glycoprotein. This amino acid sequence may be capable of specifically forming a complex with a human immunodeficiency virus envelope glycoprotein. In addition to its capability to specifically form a complex with a human immunodeficiency virus envelope glycoprotein, the amino acid sequence may be soluble in an aqueous solution.

The soluble amino acid sequence of the present invention may be used as a therapeutic agent, i.e. a prophylaxis, for the treatment of a subject infected with a human immunodeficiency virus. Moreover, a monoclonal antibody directed to the soluble amino acid sequence of the present invention may be useful as a vaccine for immunizing a human subject against a human immunodeficiency virus. Additionally, a monoclonal antibody directed against the soluble amino acid sequence of the present invention may be useful for preparing T4 glycoprotein anti-idiotypic antibodies. These T4 glycoprotein anti-idiotypic antibodies may be useful as a prophylaxis for treating a subject infected with a human immunodeficiency virus.

Cells ($5\times10^5$) where incubated with the mouse monoclonal antibodies OKT‾4B or OKT‾8, washed, and then incubated with FITC conjugated goat anti-mouse immunoglobulin. The cells were analyzed on a FACS IV Cell Sorter and plotted by a VAX 11/780 computer as cell number vs. log fluorescence. Untransformed NIH 3T3 cells and L cells gave identical cytofluorographic tracings. Fro 2.2 is a leukemic T cell line with phenotype T3⁻; T4⁺; T8⁺; T11⁺. LTD-4 is a T4⁺ primary L cell transformant obtained following transfer of total genomic DNA. 3A+ is an NIH 3T3 cell line that was transformed with the T4-pMV6tk/neo retroviral expression construct.

Figure 2:
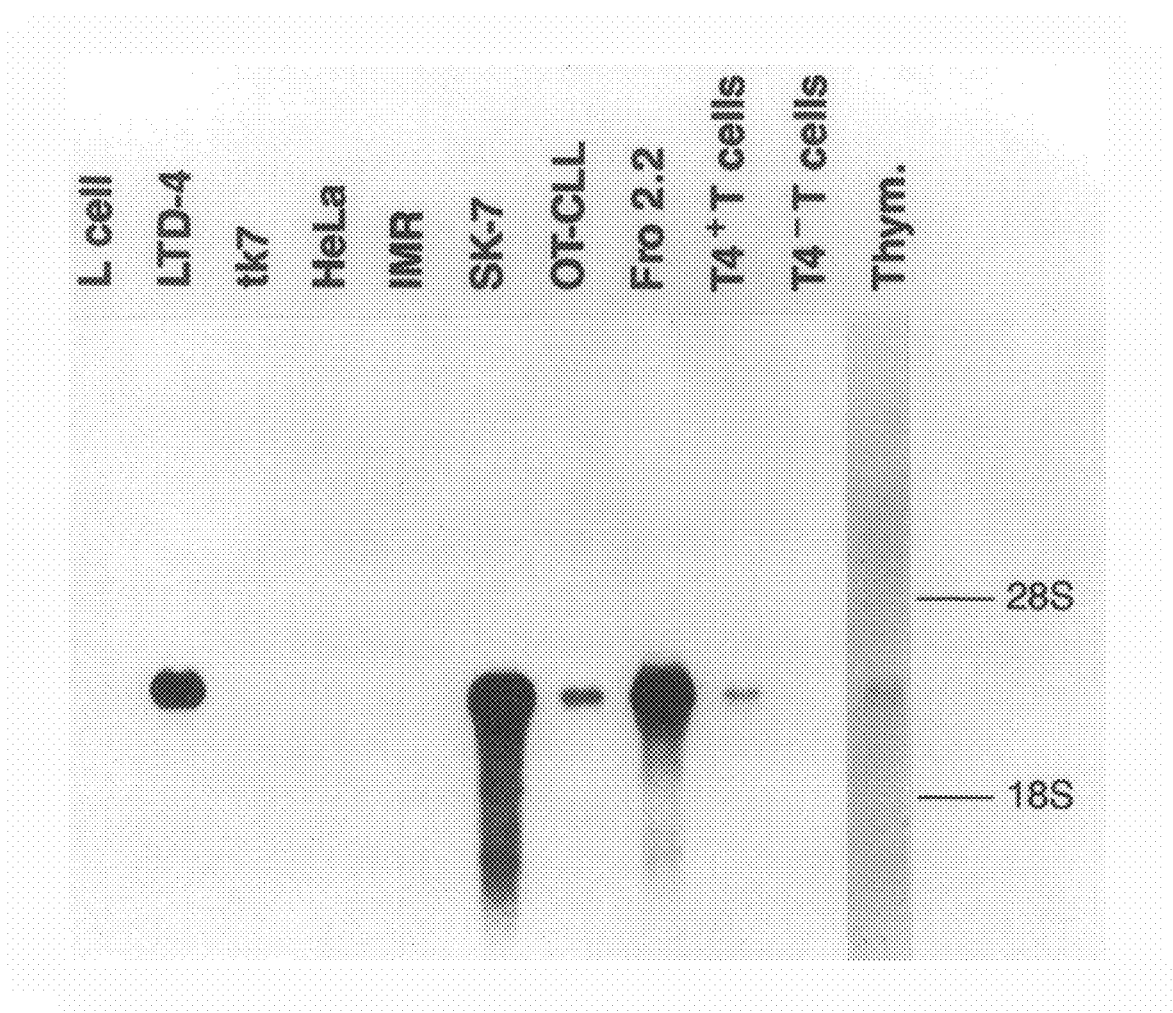

FIG. 2. Northern Blot Analysis of RNA Derived from T4⁺ and T4⁻ L Cells and Human Cells Three micrograms of poly(A)⁺ RNA or 12 $\mu$g of total RNA (peripheral T cells and thymocytes) were electrophoresed through a 0.8% agarose-formaldehyde gel, blotted onto GeneScreen (New England Nuclear), and probed with a $^{32}$P-labeled 0.6 kb T4 cDNA insert. T4⁺ cells include LTD-4 (T4⁺, T8⁻ L cell transformant), SK-7 T cell hybridoma (T4⁺, T8⁻), OT-CLL leukemia (T4⁺, T8⁻), Fro 2.2 leukemia (T4⁺, T8⁺), T4–enriched peripheral T lymphocytes, and human thymocytes. T4⁻ cells include untransformed cells, tk7 (T8⁺ L cell transformant), HeLa cells, human neuroblastoma cells (IMR), and T8-enriched peripheral T lymphocytes. The human thymocyte lane was exposed four times longer and photographed on high contrast film.

FIG. 3. Restriction Nuclease Maps of pT4B and the T4 Gene, Sequencing Strategy, and Recombinant Vectors A. Alignment of the Bam HI restriction fragments of pT4B cDNA and the T4 gene. The order of Bam HI fragments in the T4 gene was determined by Southern blot analysis and genomic clone mapping. The alignment of the 5' end of pT4B and the T4 gene is shown by dotted lines, and the shaded region in pT4B corresponds to the coding sequence. The indicated sizes are in kilobases.

B. Sequencing strategy. Arrows indicate length of sequence determined by subcloning fragments into M13 and sequencing by the dideoxy termination procedure (36).

C. Eukaryotic expression vectors. These constructs contain two Moloney murine leukemia virus long terminal repeats (LTRs) whose orientations are indicated by arrows. The pT4B cDNA was subcloned into the Eco RI site of each vector in the orientation indicated. (a) The T4-pVcos7 construct. (b) The T4-pMV6tk/neo construct contains the neomycin phosphotransferase gene fused to the HSV thymidine kinase promoter.

Figure 4:
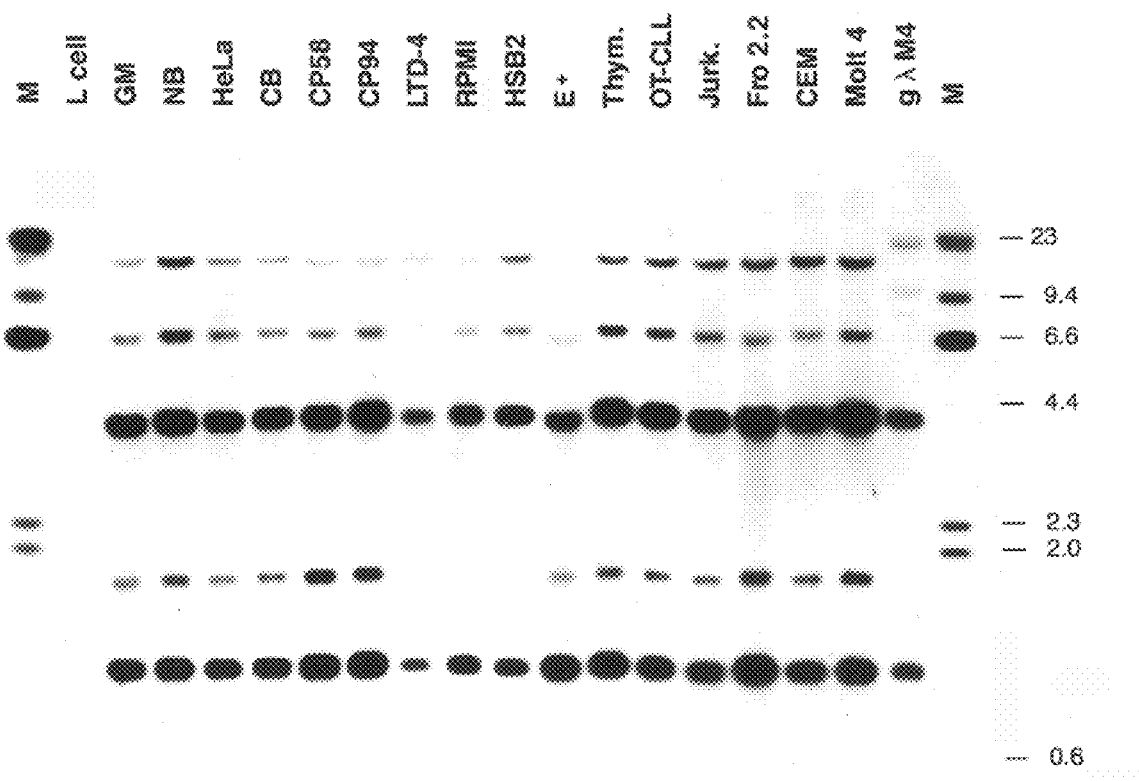

FIG. 4. Southern Blot Analysis of DNA from Untransformed and T4⁺ L Cells and T, B, and Nonlymphoid Human Cells Ten micrograms of cellular DNAs were digested with Bam HI, electrophoresed through a 0.8% agarose gel, blotted onto GeneScreen, and probed with a nick-translated pT4B cDNA insert. The indicated size markers are in kilobases. Hybridizing bands of sizes 20 kb, 6.6 kb, 4 kb, 1.8 kb, and 1 kb appear in all human DNAs. DNAs from T4⁻, nonlymphoid origin include untransformed L cells, human fibroblasts (GM), human neuroblastoma cells (NB), and HeLa cells. CB, CP58, and CP94 are DNAs derived from EBV-transformed human B cell lines. LTD-4 is the T4⁺ primary L cell transformant. RPMI and HSB2 are T4⁻ human T cell leukemic lines; E⁺ cells and thymocytes (Thym.) contain T4⁺ T cells. OT-CLL, Jurkat (Jurk.), Fro 2.2, CEM, and Molt 4 are T4⁺ T cells. g$\lambda$M4 is a genomic clone which contains sequences spanning the 3' end of the T4 gene.

Figure 5:
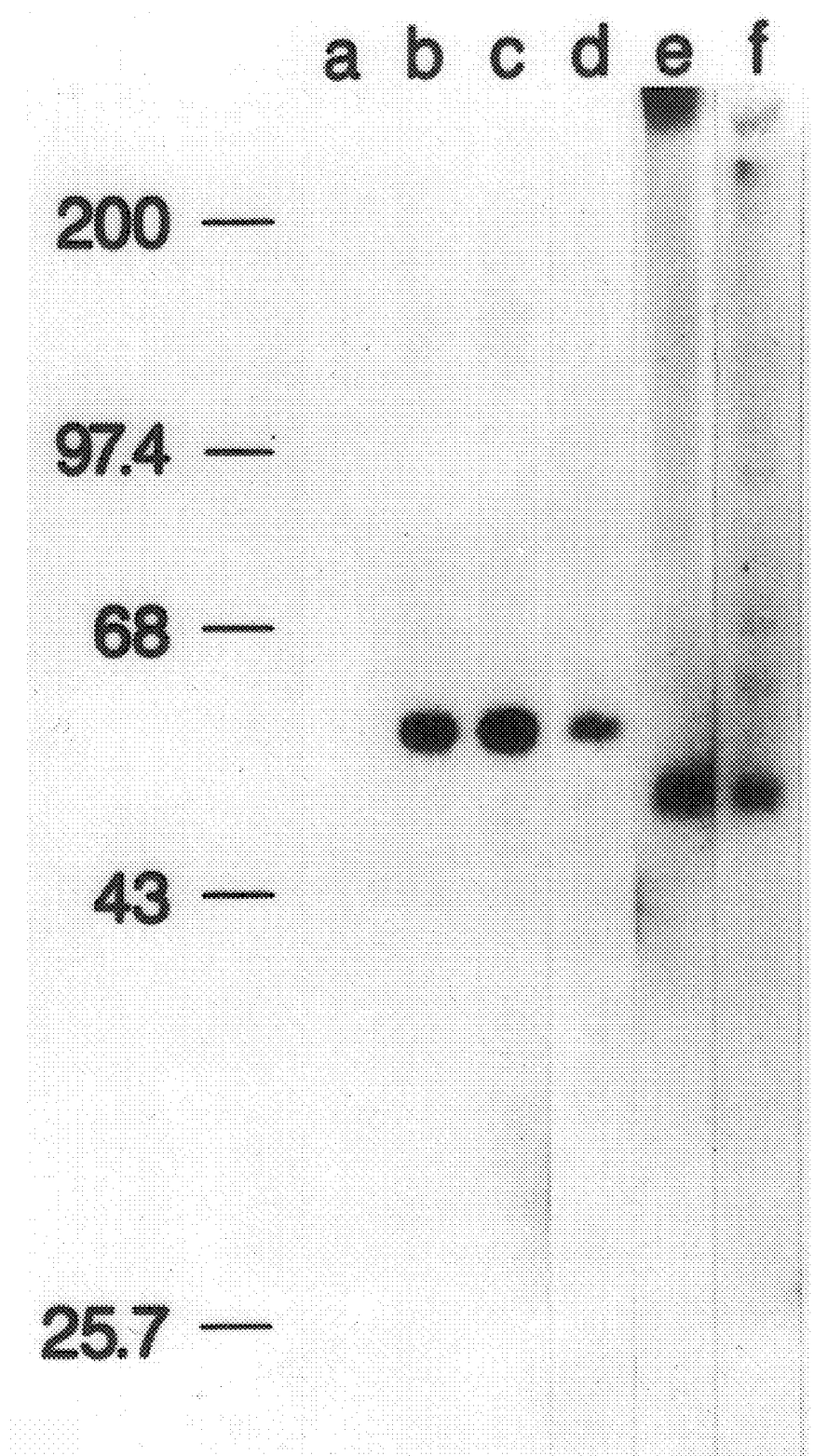

FIG. 5. Immunoprecipitation of the T4 Glycoprotein from NIH 3T3 Cells Transformed with the Retroviral Expression Constructs L-[$^{35}$S]-methionine labeled proteins from two independent NIH 3T3 transformants, peripheral T lymphocytes, and untransformed 3T3 cells were subjected to lentil lectin chromatography to enrich for glycoproteins. $2.5\times10^6$ cpm of each sample was precleared and then immunoprecipitated with OKT‾4 monoclonal antibodies and Protein A-Sepharose. The beads were washed, dissolved in sample buffer, and electrophoresed through a 10% SDS-polyacrylamide gel under reducing (lanes a–d) and nonreducing (lanes e and f) conditions. Lane a, untransformed NIH 3T3 cells. Lane b, T4C2, an NIH 3T3 cell transformed with the T4-pvcos7 construct. Lanes c and e, 3A+, an NIH 3T3 cell transformed with the T4-pMV6tk/neo construct. Lanes d and f, peripheral human T lymphocytes. Relative molecular masses ($M_r$) are given in kilodaltons.

FIG. 6. Nucleotide Sequence of the T4 cDNA and Translated Sequence of the T4 Protein FIG. 7. In Vitro Translation RNA derived from SP6 Transcription The full length T4 cDNA insert was subcloned into the RNA expression vector pSP65 (Promega Corporation). Linearized plasmid DNA was transcribed with SP6 polymerase (40), and RNA was translated into a wheat germ system (Bethesda Research Laboratories) containing L-[$^{35}$S]-methionine. The in vitro translation products were subjected to electrophoresis through a 10% SDS-polyacrylamide gel (T4). Bovine pituitary RNA (BP) was used as a control. Relative molecular masses ($M_R$) are given in kilodaltons.

Figure 8:
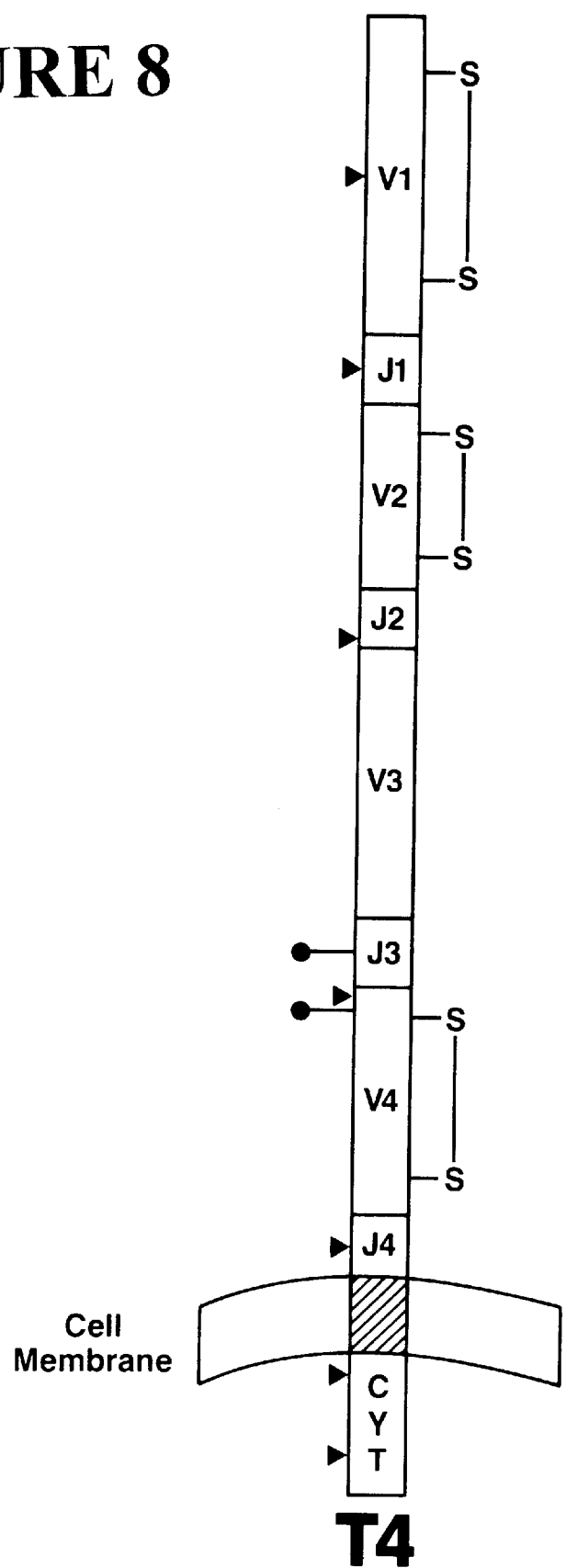

FIG. 8: Schematic diagram of the T4 glycoprotein spanning the cell membrane

T4 consists of four tandem VJ-like domains ($V_1J_1$–$V_4J_4$), a hydrophobic membrane-spanning segment (shaded area), and a charged cytoplasmic region (CYT). Two potential N-linked glycosylation sites in the extracellular portion are indicated (●——). The positions of introns 2–8 in the T4 gene are also marked (▲).

FIG. 9. Alignment of the Variable, Joining, and Transmembrane Regions of T4 with Members of the Immunoglobulin Gene Family A. Alignment of the variable region amino acid sequence of T4 (SEQ ID NO: 3) with a mouse kappa (SEQ ID NO: 4)

light chain immunoglobulin J606 (66), T8 (SEQ ID NO: 6) (20), a human T cell antigen receptor β-chain YT35 (SEQ ID NO: 7) (97), and a human T cell antigen receptor α-chain HPB-MLT (SEQ ID NO: 8) α (98). The invariant residues in the light chain variable region are included (Inv.) (SEQ ID NO: 5) in the alignment. The alignment was performed in order to maximize identities and structural homologies with T4, which appear as boxed residues. The lines below the sequence with letters A, B, C, C', D, E, F, and G indicate the residues which form β-strands (67). β-strand G continues into the J sequence.

B. Alignment of the joining region amino acid sequence of T4 with the consensus J sequences of the T cell antigen receptor β-chain, immunoglobulin lambda and kappa light chains, and the J sequence of the human T cell receptor α-chain (99).

C. Alignment of the transmembrane regions of T4 and an MHC class II βchain (100). The putative transmembrane domain (TM) is indicated below the sequence (SEQ ID NOS: 9–15).

Figure 10:
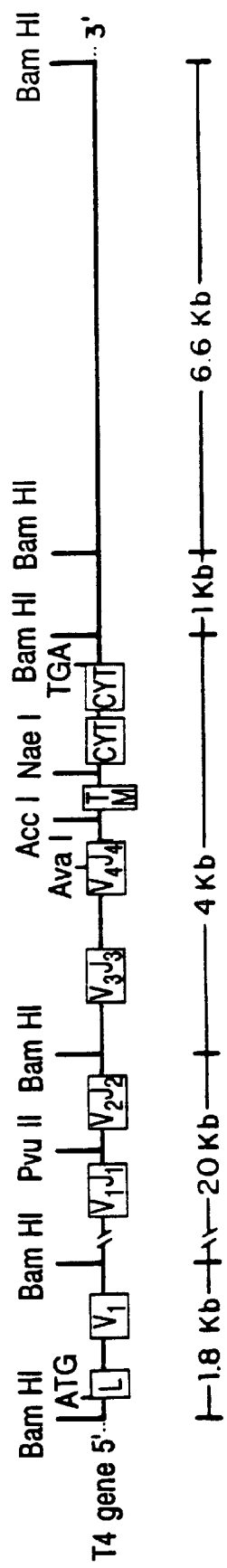

FIG. 10. Restriction nuclease map of the T4 gene in human chromosomal DNA

The positions of the 9 exons were determined by genomic clone mapping, Southern blot analysis, and nucleotide sequencing. The leader sequence (L), variable-like (V), joining-like (J), transmembrane (TM), and cytoplasmic (CYT) regions are boxed. The position of the methionine codon surrounded by the intitiation consensus sequence is indicated (ATG) at the beginning of the leader exon (L); the termination codon TGA is shown at the end of the second cytoplasmic exon (CYT). The indicated sizes are in kilobases.

Figure 11A:
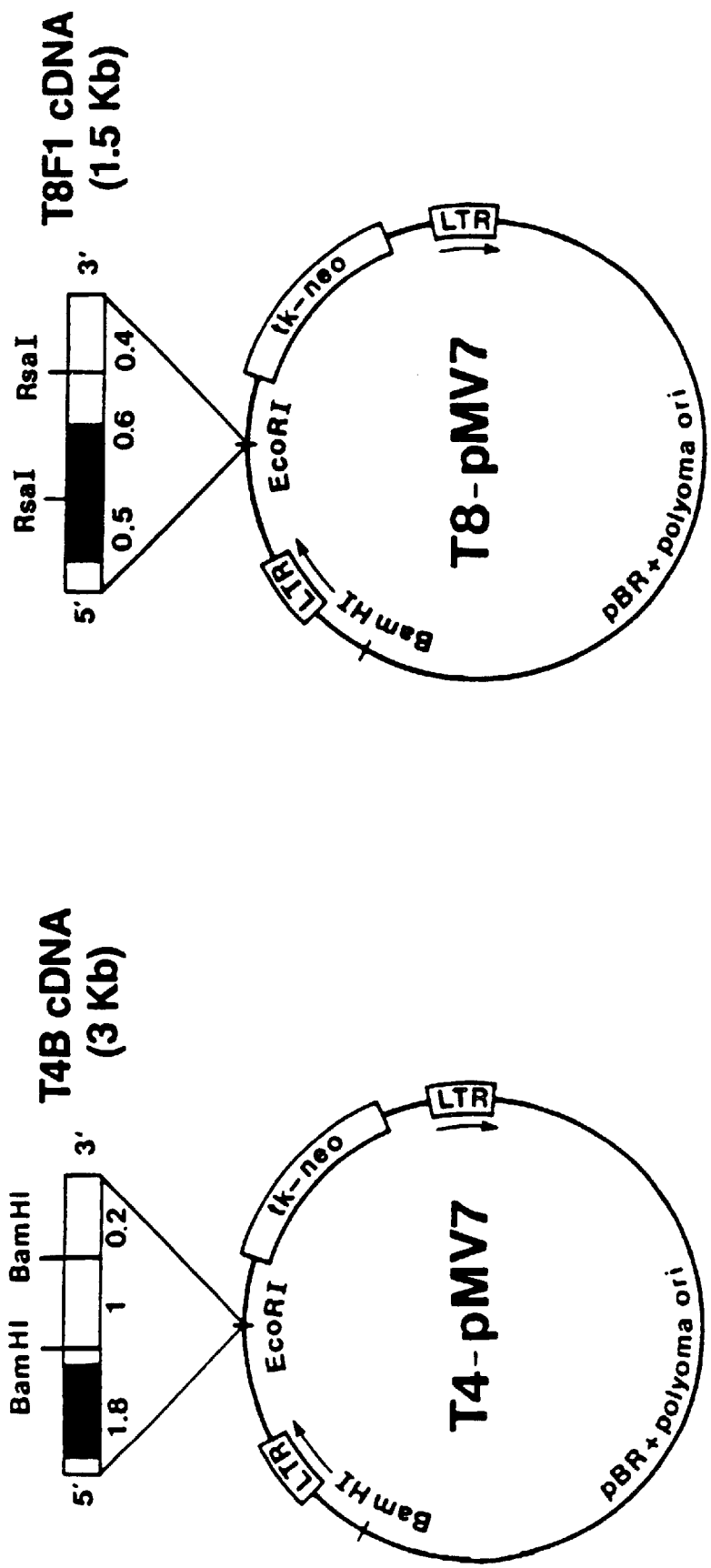

FIG. 11. Recombinant Retroviral Expression Vectors and Construction of Transformed Cells A. Recombinant retroviral expression vectors. pMV7 contains two directly repeated Moloney murine sarcoma virus long terminal repeats (LTRS) in the orientation indicated by arrows. pMV7 also contains the bacterial neomycin phosphotransferase gene (neo) fused to the HSV thymidine kinase promoter (tk). Full length cDNA inserts encoding T4 (T4B) (70) or T8 (T8F1) (20) were subcloned into the Eco RI site in the orientation indicated by arrows, generating T4-pMV7 and T8-pMV7, respectively. The coding sequences are shown as shaded regions. The indicated sizes are in kilobases.

B. Retrovirus-Mediated Gene Transfer Strategy.

Figure 12:
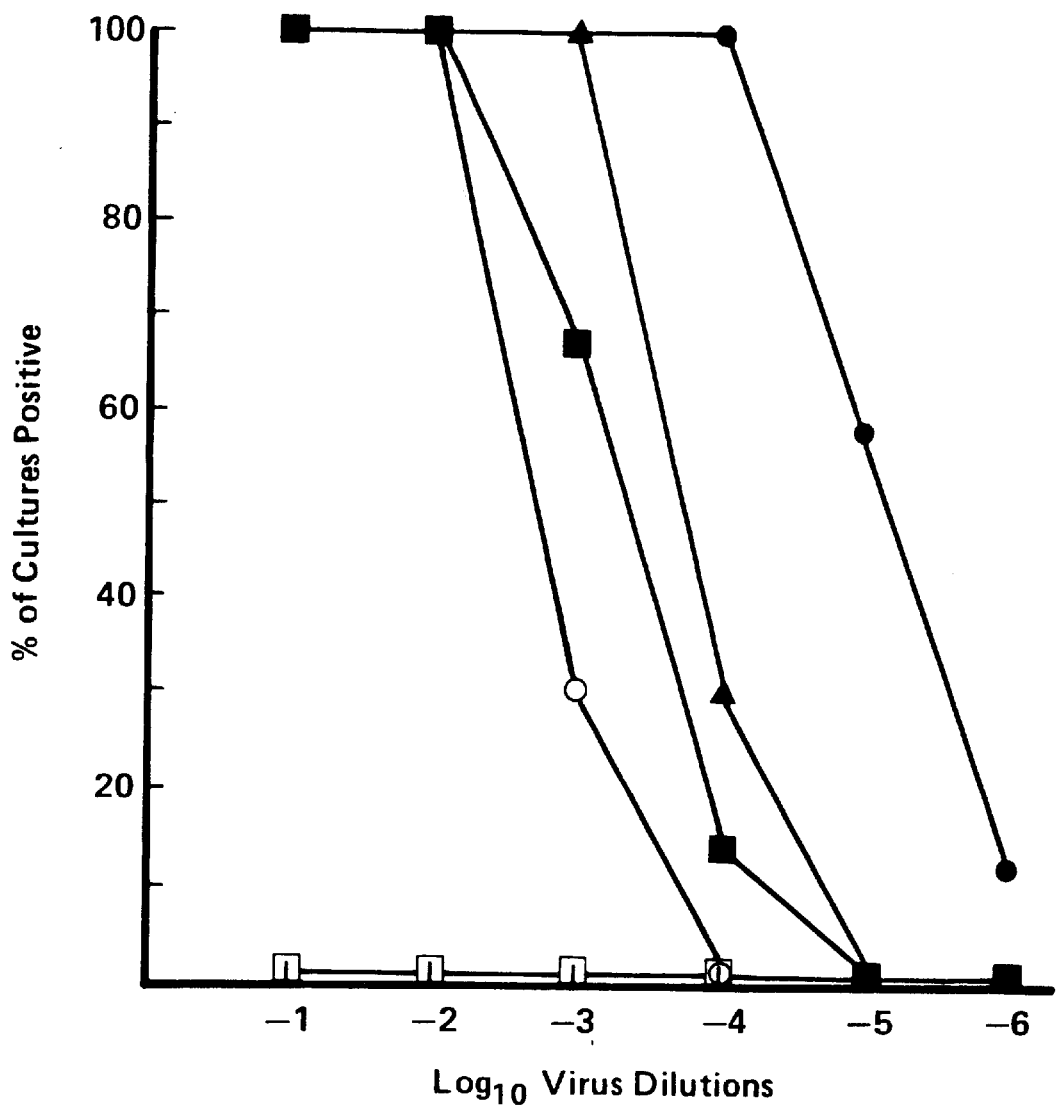

FIG. 12 The Efficency of Infection of Naturally-Isolated and Transformed T4+ Cells Cells were inoculated with serial 10-fold dilutions of AIDS virus, incubated for 18 hours at 37° C., washed, and plated in microculture. The frequency of infected cultures was determined by an enzyme-linked immunoabsorbent assay (ELISA) 12 days post-infection (46). The results were plotted as % positive cultures vs. log virus dilution. Infectious virus titer (ID-50) is defined as the reciprocal of the dilution at which 50% of the cultures are positive for virus (47). Naturally isolated T4+ cells include phytohemagglutinin (PHA)-stimulated normal peripheral lymphocytes (●——●)and the T cell line CEM (o——o). T4+ transfected cell lines include HSB2-T4+ T cells (▲——▲)and Raji-T4+ B cells (■——■). The T8+ transfected cell lines HSB2-T8+ and Raji-T8+ (□——□)served as controls in these studies.

Figure 13A:
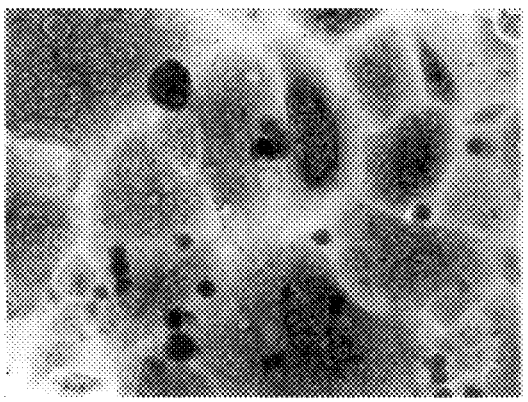
Figure 13B:
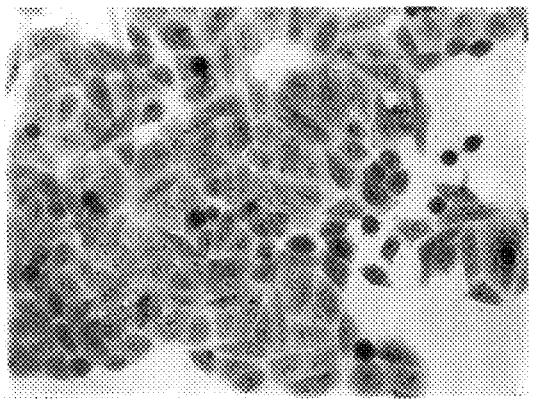

FIG. 13. Formation of Syncytia in T4+ HeLa Tranformants

A. $2 \times 10^5$ monolayer HeLa-T4+ tranformants were mixed with $2 \times 10^4$ AIDS virus-producing H9 cells and incubated at 37° C. Inspection of the cultures after 18 hours revealed that over 90% of nuclei in the monolayer sheet were contained within syncytia.

B. Anti-T4A monoclonal antibody (1:20) was added to the mixed cultures at the time of seeding. Inspection of the cultures after 18 hours revealed a complete absence of cell fusion.

Cultures were photographed at 160×magnification.

Figure 14:
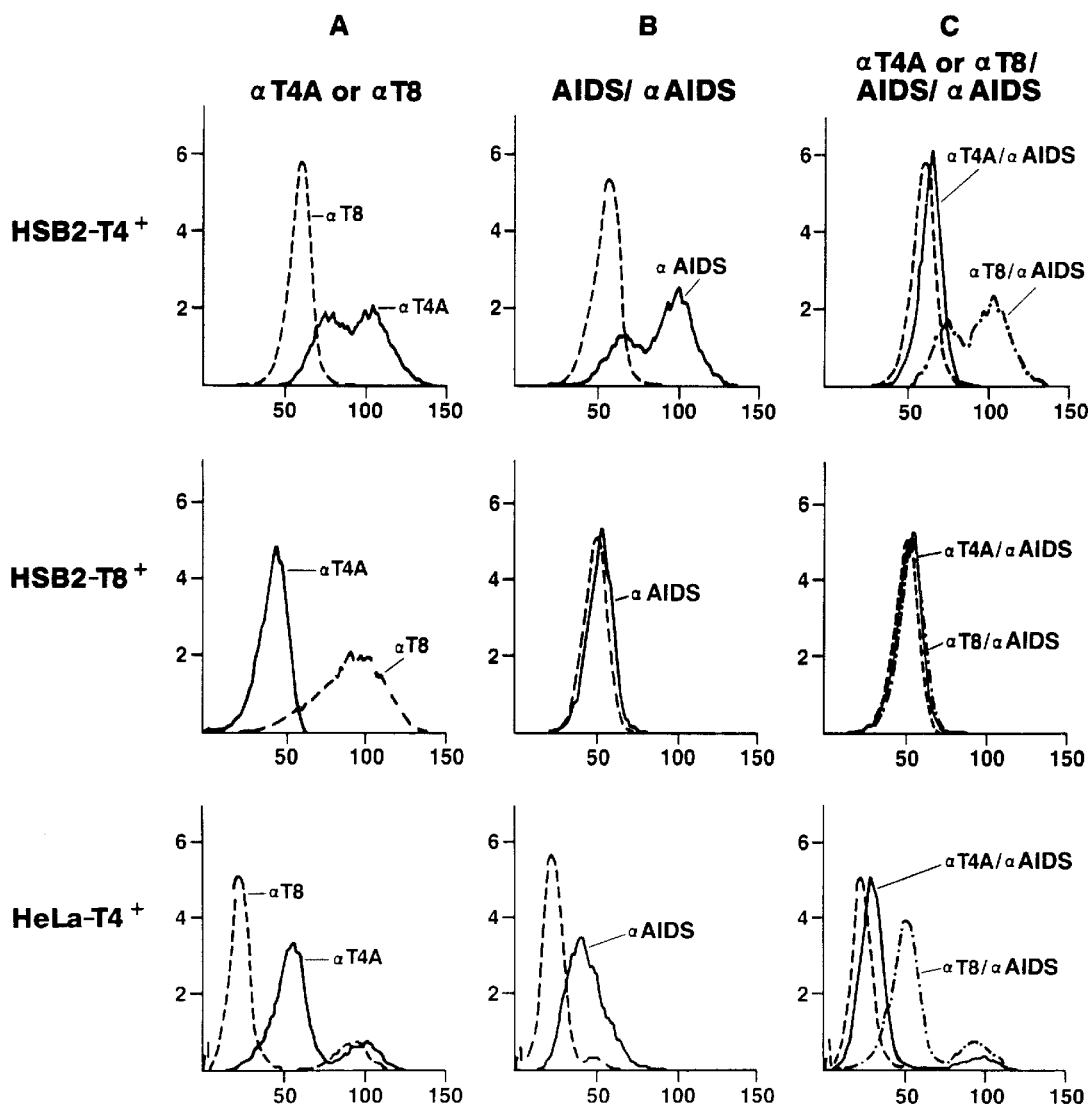

FIG. 14. Flow Cytometry Analysis of AIDS Virus binding to T4+ Transformed Cells

Column A. Cells ($5 \times 10^5$) were incubated with fluorescein-conjugated anti-T4A (-) or anti-T8 (---) monoclonal antibodies, washed, and analyzed by cytofluorometry.

Column B. Cells ($5 \times 10^5$) were incubated with buffer (---), or AIDS virus (-), washed, incubated with fluorescein-conjugated anti-AIDS virus antibody, and analyzed by cytofluorometry.

Column C. Cells ($5 \times 10^5$) were incubated with buffer (---), or with anti-T4A monoclonal antibody followed by AIDS virus (-) , or with anti-T8 monoclonal antibody followed by AIDS virus (-.-.-.). After a wash, fluorescein-conjugated anti-AIDS virus antibody was added and the cells were analyzed by cytofluorometry.

Flouorescence histograms (cell number vs. fluorescence intensity) of each cell line are arranged horizontally.

FIG. 15. Northern Blot Analysis of RNA Derived from Human and Mouse Brain, Lymphoid, and Myeloid Cells A. Northern blot analysis of human RNA samples. One microgram of poly(A)+ RNA from Raji (T4− B cell line), U937 (T4+ monocytic cell line), and Jurkat (T4+ T cell line), and five micrograms of poly(A)+ RNA from cerebral cortex, were electrophoresed through a 1% agarose-formaldehyde gel, blotted onto Hybond (Amersham), and probed with a $^{32}$P-labelled T4 cDNA insert, pT4B (70).

B. Northern blot analysis of mouse RNA samples. Five micrograms of poly(A)+ RNA from 3T3 cells (fibroblast cell line), forebrain, and hindbrain, and 20 micrograms of total RNA from thymocytes, were eletrophoresed through a 1% agarose-formaldehyde gel, transferred onto Hybond, and probed with a $^{32}$P-labelled L3T4 cDNA insert, pL3T4B.

The cDNA clone pT4B was deposited pursuant to and in satisfaction of, the requirements of the Budapest Treaty on the International Recognition of the Deposit of Microorganisms for the Purposes of Patent Procedure with the American Type Culture Collection (ATCC), 10801 University Boulevard, Manassas, Va. 20110-2209 on Aug. 21, 1990 under ATCC Accession No. 68389.

DETAILED DESCRIPTION OF THE INVENTION

A single-stranded nucleic acid molecule is provided which encodes an amino acid sequence comprising at least a portion of a T4 glycoprotein. In one embodiment of the invention, the nucleic acid molecule encodes an amino acid sequence capable of specifically forming a complex with a human immunodeficiency virus envelope glycoprotein. In another embodiment of the invention, the nucleic acid molecule is at least 90% homologous to a nucleic acid molecule which encodes an amino acid sequence which is at least a portion of a T4 glycoprotein. In still another embodiment of the invention, the nucleic acid molecule encodes an amino acid sequence which, in addition to its capabililty of specifically forming a complex with a human immunodeficiency virus envelope glycoprotein, is soluble in an aqueous solution. Within this application "aqueous solution" includes, but is not limited to, detergent-free aqueous buffers and body fluids such as blood, plasma and serum. Additionally, "soluble T4" means a fragment of a T4 glycoprotein which is soluble in an aqueous solution. In a further embodiment of the invention, the nucleic acid molecule encodes an amino acid sequence which is at least a portion of a human T4 glycoprotein.

Also provided is a nucleic acid molecule which is complementary to a single-stranded nucleic acid molecule encoding an amino acid sequence comprising at least a portion of a T4 glycoprotein. This complementary nucleic acid molecule may be labeled with a detectable marker. Such detectable markers are known in the art to which this invention pertains and include detectable enzymes, radiolabeled moieties, fluorescent moieties, and chemiluminescent moieties.

The single-stranded nucleic acid molecule may be a DNA molecule. In one embodiment of the invention, the DNA molecule comprises at least a portion of the genomic DNA molecule represented by the restriction enzyme map shown in FIG. 10. In another embodiment of the invention, the single-stranded nucleic acid molecule may be a cDNA molecule which comprises at least a portion of the nucleic acid sequence shown in FIG. 6. In a specific embodiment of the invention, the cDNA molecule encodes an amino acid sequence capable of specifically forming a complex with a human immunodeficiency virus envelope glycoprotein and soluble in an aqueous solution. This cDNA molecule comprises at least a portion of the nucleic acid sequence shown in FIG. 6.

The present invention further provides an RNA molecule which encodes an amino acid sequence comprising at least portion of a T4 glycoprotein.

A method for detecting a single-stranded nucleic acid molecule encoding an amino acid sequence which is at least a portion of a T4 glycoprotein is provided by the present invention. This method comprises contacting single-stranded nucleic acid molecules with a labeled, single-stranded nucleic acid molecule which is complementary to a single-stranded nucleic acid molecule encoding an amino acid sequence which is at least a portion of a T4 glycoprotein, under conditions permitting hybridization of complementary single-stranded nucleic acid molecules. Hybridized nucleic acid molecules are separated from single-stranded nucleic acid molecules to detect a single-stranded nucleic acid molecule which encodes an amino acid sequence which is at least a portion of a T4 glycoprotein. In one embodiment of the invention, the detected single-stranded molecule is a DNA molecule derived fran chromosomal DNA. The chromosomal DNA may be derived from lymphoid, myeloid or brain cells. The lymphoid cell may be a T cell or a B cell. Furthermore, the myeloid cell may be a granulocyte site or a macrophage.

The present invention also provides an amino acid sequence which comprises at least a portion of a T4 glycoprotein. In one embodiment of the invention, the amino acid sequence is capable of specifically forming a complex with a human immunodeficiency virus envelope glycoprotein. In another embodiment of the invention, the amino acid sequence is at least 90% homologous to a portion of a T4 glycoprotein and is capable of specifically forming a complex with a human immunodeficiency virus envelope glycoprotein. In yet a further embodiment of the invention, the amino acid sequence which is at least 90% homologous to a portion of a T4 glycoprotein, in addition to its capability of specifically forming a complex with a human immunodeficiency virus envelope glycoprotein, is soluble in an aqueous solution.

Also provided is a peptide which comprises at least one amino acid sequence of the present invention which is a portion of a T4 glycoprotein. A polypeptide which comprises at least two of these peptides is also provided.

In one embodiment of the invention, the amino acid sequence which is capable of specifically forming a complex with a human immunodeficiency virus envelope glycoprotein and which is soluble in an aqueous solution is useful as a therapeutic agent for the treatment of a subject infected with a human immunodeficiency virus, i.e. as a prophylaxis for AIDS. In a preferred embodiment of the invention, the amino acid sequence comprises the amino acid sequence shown in FIG. 6 from at least amino acid −23 to at most amino acid +374. Other preferred embodiments of the invention include amino acid sequences which comprise the amino acid sequence shown in FIG. 6 from at least amino acid +287 to at most amino acid +374, from at least amino acid +182 to at most amino acid +286, from at least amino acid +112 to at most amino acid +181, and from at least amino acid +1 to at most amino acid +111.

A pharmaceutical composition useful as a therapeutic agent for the treatment of a subject intected with a human immunodeficiency virus is also provided. This pharmaceutical composition comprises an amino acid sequence of the present invention which is capable of specifically forming a complex with a human immunodeficiency virus envelope glycoprotein and is soluble in an aqueous solution and a pharmaceutically acceptable carrier. Such pharmaceutically acceptable carriers are known in the art to which the present invention pertains and include, but are not limited to, 0.01–0.1M, preferably 0.05 M, phosphate buffer or 0.8% saline.

A method for treating a subject intected with a human immunodeficiency virus is also provided. This method comprises administering to the subject an effective amount of a pharmaceutical composition containing a pharmaceutically acceptable carrier and an amino acid sequence of the present invention, capable of specifically forming a complex with a human immunodeficiency virus envelope glycoprotein and soluble in an aqueous solution, so as to render human immunodeficiency viruses (also referred to herein as AIDS viruses) with which the subject is infected incapable of infecting T4+ cells.

The present invention also provides a purified polypeptide encoded by a cDNA molecule which comprises at least a portion of the nucleic acid sequence shown in FIG. 6.

Further provided is a vector which comprises a cDNA molecule which is at least a portion of the nucleic acid sequence shown in FIG. 6. In one embodiment of the invention, the vector comprises a plasmid. In another embodiment of the invention, the vector comprises a virus.

A host vector system for the production of an amino acid sequence which is at least a portion of a T4 glycoprotein is also provided by the present invention. This host vector system comprises a plasmid of the present invention in a suitable host. In one embodiment of the invention, the suitable host is a bacterial cell. In another embodiment of the invention, the bacterial cell is an *Escherichia coli* cell. In yet another embodiment of the invention, the suitable host a eucaryotic cell. In a further embodiment of the invention, the eucaryotic cell is a mammalian cell. In yet a further embodiment of the invention, the eucaryotic cell is a yeast cell. In still another embodiment of the invention, the suitable host is an insect.

A method for producing an amino acid sequence which is at least a portion of a T4 glycoprotein is further provided. This method comprises growing a host vector system of the present invention under suitable conditions permitting production of at least a portion of a T4 glycoprotein, and recovering the resulting portion of a T4 glycoprotein. The present invention further provides host vector systems and methods for producing an amino acid sequence which is at least a portion of a T4 glycoprotein wherein the vector comprises a cDNA molecule of the present invention and a virus. Suitable hosts include, but are not limited to, bacterial cells, e.g. *Escherichia coli* cells, eucaryotic cells, e.g. mammalian and yeast cells, and insects. An amino acid sequence which is at least a portion of a T4 glycoprotein may be produced by growing a host vector system which comprises a virus and a cDNA molecule of the present invention under suitable conditions permitting production of at least a portion of T4 glycoprotein. The resulting portion of a T4 glycoprotein may be recovered from the host vector system by methods known in the art.

The present invention also provides a substance capable of forming a complex with an amino acid sequence which is capable of specifically forming a complex with a human immunodeficiency virus envelope glycoprotein and is soluble in an aqueous solution. In one embodiment of the invention, the substance is an antibody. In another embodiment of the invention, the antibody is a monoclonal antibody. In yet a further embodiment of the invention, the monoclonal antibody is a human monoclonal antibody.

Also provided is a vaccine useful for immunizing a human subject against a human immunodeficiency virus. This vaccine comprises a monoclonal antibody of the present invention and a pharmaceutically acceptable carrier. By administering to a human subject an effective immunizing amount of a vaccine of the present invention, the production of antibodies capable of neutralizing human immunodeficiency viruses may be invoked, thereby immunizing the subject against a human immunodeficiency virus.

Also provided is a substance capable of specifically forming a complex with a monoclonal antibody of the present invention. In one embodiment of the invention, the substance is capable of additionally forming a specific complex with a human immunodeficiency virus envelope glycoprotein. In a preferred embodiment of the invention, the substance comprises a T4 glycoprotein anti-idiotypic antibody which contains an "internal image" of the T4 binding domain capable of recognizing the receptor binding domain of a human immunodeficiency virus envelope glycoprotein.

A pharmaceutical composition is provided which comprises a T4 glycoprotein anti-idiotypic antibody of the present invention and a pharmaceutically acceptable carrier. Further provided is a method for treating a subject infected with a human immunodeficiency virus by administering to the subject an effective amount of the pharmaceutical composition of the present invention which comprises a T4 glycoprotein anti-idiotypic antibody and a pharmaceutically acceptable carrier so as to render human immunodeficiency viruses with which the subject is infected incapable of infecting T4$^+$ cells.

The various prophylaxis and immunization methods for AIDS provided by the present invention are based upon the abilities of the novel peptides, antibodies, and DNA molecules disclosed herein to form complexes with, or hybridize to, specific molecules and to invoke an immunological response effective for neutralizing the AIDS virus. These molecules, methods for their preparation, and methods of AIDS treatment will be better understood by reference to the following experiments and examples which are provided for purposes of illustration and are not to be construed as in any way limiting the scope of the present invention, which is defined by the claims appended hereto.

Materials and Methods

Cells and Antibodies

Peripheral blood leukocytes isolated by Ficoll-Hypaque density gradient centrifugation were fractionated into sheep erythrocyte rosette-positive (E$^+$) cells. T4$^+$ and T8$^+$ subsets within the E$^+$ population were isolated by positive selection of T8-bearing cells with anti-T8 antibody and human erythrocytes conjugated with affinity-purified rabbit anti-mouse IgG (10). Cytofluorometric analysis of these subsets demonstrated that the T4$^+$ cells were >95% T4$^+$ and <2% T8$^+$, whereas the T8$^+$ cells were >95% T8$^+$ and <2% T4$^+$.

The Fro 2.2 T cell line (T3$^-$, T4$^+$, T8$^+$, T11$^+$) was derived from an adult patient with undifferentiated acute leukemia. Jurkatt is T3$^-$, T4$^+$, T8$^+$, T11$^-$, RPMI 8402 is T3$^-$, T4$^-$, T8$^-$, T11$^+$. OT-CLL is a chronic lymphocytic leukemia which is T3$^+$, T4$^+$, T8$^-$, and T11$^+$ (22). The T4$^+$ cell lines CEM and Molt 4 were obtained from the American Type Culture Collection. All leukemic T cell lines were continuously grown in RPMI 1640 medium containing 5% fetal calf serum. Transformed B cell lines CB, CP58 and CP94 were derived as previously described (23).

Affinity-purified rabbit anti-mouse IgG was conjugated to human erythrocytes by the chromium chloride method (24).

Cotransformation of L Cells and NIH 3T3 Cells

Murine L tk$^-$aprt$^-$ cells were maintained in Dulbecco's modified Eagle's medium (DME) supplemented with 10% calf serum (Gibco) and 50 micrograms/ml diaminopurine (DAP). L cells were plated out at a density of 5×10$^4$ cells per 10 cm dish, 1 day before transformation. Calcium phosphate precipitates were prepared by the method of Graham and van der Eb (25), as modified by Wigler et al. (26), using 100 ng of pTK and 20 micrograms of high molecular weight T cell or L cell DNA per dish. The L cells were placed under selection in DME with 10% calf serum, 15 micrograms/ml hypoxanthine, 1 microgram/ml aminopterin and 5 micrograms/ml thymidine (HAT medium (27)) on the following day. After 12–14 days of HAT selection, tk$^+$ transformants were screened using the rosetting assay.

Murine NIH 3T3 cells were maintained in DME supplemented with 10% newborn calf serum (Gibco). NIH 3T3 cells were plated out at a density of 5×10$^4$ cells per 10 cm dish, 2 days before transformation. A calcium phosphate precipitate was applied to the cells using 10 micrograms of carrier DNA and either 10 micrograms of T4-pMV6tk/neo or 10 micrograms of T4-pVcos7 and 500 ng of pSV2neo. After 2 days, the cells were placed under selection in DME with 10% calf serum and 500 micrograms/ml G418 (Geneticin*; Gibco). Rosetting assays were performed on surviving colonies one week after growth in selective medium.

Rosetting Assay

After one rinse with phosphate-buffered saline (PBS), the plates were incubated with 2.5 ml of the purified monoclonal antibody OKT$^-$4A (1 mg/ml) diluted at 1/500 in PBS containing 5% fetal calf serum for 45 minutes at room temperature. Free antibody was removed from the plates with three gentle rinses in PBS. Six milliliters of human erythrocytes conjugated with purified rabbit anti-mouse IgG antibody (2% v/v stock suspension, diluted 1/10 in PBS/5% fetal calf serum) were added and the plates were left at room temperature. After 45 minutes, free erythrocytes were gently aspirated and PBS was added prior to inspection for rosette-positive colonies.

Cytofluorometric Analysis

Adherent cells were removed with 0.005 M EDTA in PBS and washed once with PBS containing 1% bovine serum albumin (BSA) and 0.01% sodium azide (cytowash). Cells ($5\times10^6$) in 0.1 ml were added to tubes with appropriate dilutions of OKT4, OKT8 or control antibodies. The cell-antibody mixture was incubated for 45 minutes at 4° C. and then washed twice in cytowash. Fluoroscein isothiocyanate (FITC)—conjugated goat anti-mouse immunoglobulins (IgG+IgA+IgM)(Cappel) was added to the cells and incubated for 1 hour at 4° C. The cells were then washed three times in cytowash and resuspended in 0.5 ml of PBS with 0.01% sodium azide. The cells were analyzed on a Becton Dickinson FACS-IV Cell Sorter and the data was stored and plotted using a VAX 11/780 computer (Digital Equipment Co.)

RNA and DNA Isolation

Total RNA was isolated from cells by homogenation in 4 M guanidinium thiocyanate, followed by ultracentrifugation through a 5.7 M CsCl cushion (28). Poly(A)$^+$ selection was achieved by oligo(dT)-cellulose chromatography (Type 3, Collaborative Research) (29). High molecular weight genomic DNA was prepared as described by Wigler et al. (26).

cDNA and Genomic Libraries

Double-stranded cDNA was synthesized from poly(A)$^+$ RNA derived from peripheral human T cells (20). After treatment with EcoRI methylase and T4 DNA polymerase, the double-stranded cDNA was cloned into the EcoRI site of λ gt10 (30) using EcoRI linkers. The Charon 4 human genomic library was generously provided by Dr. Tom Maniatis (Harvard University) (31).

Synthesis of a Subtracted cDNA Probe $^{32}$P-labeled cDNA was synthesized from poly(A)$^+$ RNA derived from the primary transformant, LTD-4, as described by Davis et al. (32). After annealing the cDNA to an excess of untransformed L cell poly(A)$^+$ RNA (Rot =3000), single-stranded sequences, which were enriched for human cDNAs, were isolated by hydroxyapatite chromatography (32). Prior to filter hybridization, the subtracted cDNA probe was concentrated with sec-butanol and desalted on a G-50 Sephadex column equilibrated in TE.

Screening of cDNA and Genomic Libraries

The peripheral human T cell library was plated on *E. coli* C600/HFL and the human genomic library was plated on *E. coli* LE392. Screening of duplicate filters was carried out according to the standard procedure (33), with the hybridization performed in 50% formamide and 5×SSC at 42° C. In the screen of the cDNA library, $6\times10^4$ cpm of subtracted probe was applied per 137 mm nitrocellulose filter. Filters from the genomic library were hybridized to a nick-translated (34) cDNA insert. The washes were performed at 68° C., with a final wash in 0.2×SSC. Autoradiography was performed at –70° C. in the presence of intensifying screens for 1–2 days.

DNA Sequencing

Figure 3A:
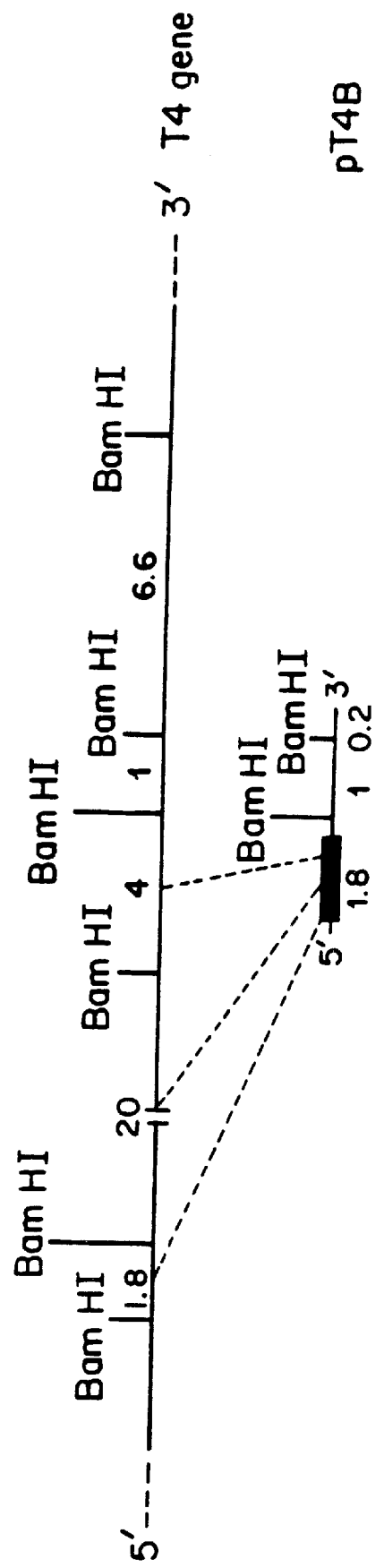
Figure 3B:
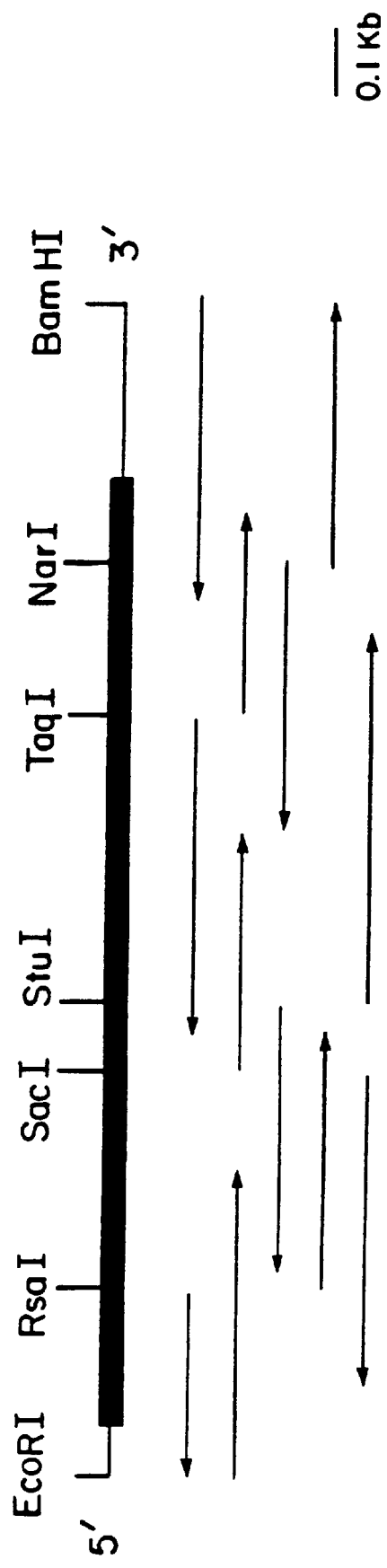

Restriction fragments of pT4B were subcloned into the M13 vectors mp18 and mp19 (35). Sequencing reactions were performed using the dideoxy chain termination technique (36). The sequencing strategy is depicted in FIG. 3B.

Southern and Northern Blot Hybridizations

High molecular weight cellular DNAs were digested with 5 units of restriction nuclease per microgram of DNA according to the manufacturer's recommendation (Boehringer Mannheim). Samples (10 micrograms) were subjected to electrophoresis on a 0.8% agarose gel. DNA fragments were transferred to GeneScreen (New England Nuclear; (37)) and hybridized as described by Church and Gilbert (38).

RNA was run on a 0.8% agarose-formaldehyde gel (39) and transferred to GeneScreen. Northern hybridization was performed according to the procedures supplied by the manufacturer. Both Southern and Northern blots were hybridized to nick-translated probes.

Synthesis and In Vitro Translation of SP6 RNA

The 3 kb T4 cDNA was subcloned into the EcoRI cite of pSP65 (Promega Corporation) and linearized with HindIII. Transcription of linearized plasmid DNA (1 microgram) with SP^ polymerase in the absence of radiolabeled nucleotides was performed as described (40), except that GpppG and unlabeled CTP were added to the transcription buffer. One-tenth of the reaction mixture was translated in a wheat germ system (Bethesda Research Laboratories) containing L-[$^{32}$S]-methionine (Amersham) and 1 micromolar S-adenosylmethionine. The in vitro translation products were subjected to SDS-polyacrylamide electrophoresis under reducing conditions as described below.

Cell Labeling, Lectin Chromatography and Immunoprecipitation

Cells were grown for 12 hours in methionine-free DME medium containing 10% dialyzed calf serum and 1 mCi of L-[$^{32}$S]-methionine (Amersham) as previously described (41). The cells were solubilized in 10 mM Tris (pH 7.4), 150 mM NaCl (TBS) containing 0.5% Nonidet P-40 (Shell) and 0.2 mM phenylmethylsulfonyl fluoride (Sigma). The lysates were centrifuged for 1 hour at 100,000×g, and the supernatants were subjected to lentil lectin chromatography (Pharmacia) according to the procedures of Hedo et al. (42). Eluates were pre-absorbed once with a mixture of control mouse ascites and protein A-Sepharose (Pharmacia) for 1 hour at 4° C. and twice with protein A-Sepharose alone for 1 hour at 4° C. Of each supernatant, $2.5\times10^4$ cpm were then mixed with 10 microliters monoclonal antibody (approximately 1 mg/ml) and protein A-Sepharose and incubated on a turntable overnight at 4° C. The beads were then washed four times with cold TBS containing 0.5% NP-40 and 0.2% SDS and were resuspended in electrophoresis sample buffer.

Gel Electrophoresis

SDS-polyacrylamide gel electrophoresis was performed according to the procedure of Laemmli (43). The immunoprecipitates and in vitro translation products were dissolved in sample buffer with or without 2-mercaptoethanol and then were applied to 10% polyacrylamide gels. Autoradiography was performed on Kodak XAR-5 film in the presence of intensifying screens (DuPont Chemical Company).

Cotransformation and Rosetting Assay

Mouse Ψ-2 cells (44) were maintained in Dulbecco's modified Eagle's medium (DME) supplemented with 10% calf serum (CS) (Gibco). Ψ-2 cells were plated out at a density of $5\times10^5$ cells per 10 cm dish, 2 days before transformation. Calcium phosphate precipitates were prepared by the method of Graham and van der Eb (25), as modified by Wigler et al. (27). Precipitates were applied to the cells using 10 micrograms of carrier DNA and either 10 micrograms of T4-pMV7 or 10 micrograms of T8-pMV7. After 2 days, the cells were placed under selection in DME/10% CS and 500 micrograms/ml G418 (Geneticin; Gibco).

Rosetting assays to identify T4$^+$ or T8$^+$ colonies were performed on surviving colonies 1 week after growth in selective medium. After one rinse with phosphate-buffered saline (PBS), the plates were incubated with 2.5 ml of the purified monoclonal antibody OKT4A or OKT8 (1 mg/ml; Ortho) diluted at 1/500 in PBS containing 5% fetal calf serum (FCS) for 45 minutes at room temperature. Free antibody was removed from the plates with three gentle rinses in PBS. 6 ml of human erythrocytes conjugated with purified rabbit anti-mouse IgG antibody (2% v/v stock suspension, diluted $\frac{1}{10}$ in PBS/5% FCS) were added and the plates were left at room temperature. After 45 minutes, free erythrocytes were gently aspirated and PBS was added prior to inspection. $T4^+$ and $T8^+$ $\Psi$-2 clones were purified by colony isolation and characterized by flow cytometry and Northern blot analysis.

Recombinant Retrovirus Production and Infection $T4^+$ and $T8^+$ $\Psi$-2 clones were isolated which produce recombinant retrovirus stocks with titers of $10^5$ cfu/ml. Viral stocks were prepared by adding 10 ml of fresh DME/10% CS to a near confluent monolayer of the $T4^+$ or $T8^+$ $\Psi$-2 clones. After 24 hours, the medium was removed and filtered through a 0.45 micrometer filter (Millipore). For infection, $5 \times 10^5$ cells were incubated with 2 ml of viral supernatant (or a dilution) in the presence of 8 micrograms/ml polybrene (Aldrich). After 3 hours, 8 ml of fresh medium was added. 3 days after infection the cells were reseeded into DME/10% CS containing 500 micrograms/ml G418, grown for 2 weeks, scored for $G418^r$ colonies, and screened for surface T4 or T8 expression using the in situ rosetting procedure or flow cytometry.

$\Psi$-2 culture supernatants were used to infect mouse $\Psi$-AM cells as described above. $T4^+$ or $T8^+$ adherent transformants were purified by the in situ resetting assay followed by colony isolation; $T4^+$ or $T8^+$ non-adherent transformants were purified by fluorescence-activated cell sorting (FACS). Non-adherent human lymphoid cell lines (HSB2, RPMI-T cells; Raji-B cells) and adherent epithelial cells (HeLa) were infected by co-cultivation with $T4^+$ or $T8^+$ $\Psi$-AM clones (pretreated with 10 micrograms/ml mitomycin-C for 2 hours; Sigma) and were purified.

Cell lines were selected for G418 resistance at a concentration of 1.5 mg/ml, except for HeLa cells which require 1 mg/ml, and fibroblasts which require 0.5 mg/ml. All cell cultures producing recombinant amphotrophic viruses ($\Psi$-AM) were maintained under P3 containment conditions.

AIDS Virus

The prototype LAV strain of HTLV-III/LAV was obtained from J.-C. Cherman (Institut Pasteur, Paris; (45)). Virus inocula used in these studies were from the second to fifth passages of virus in our laboratory. Inocula are culture supernatants from HTLV-III/LAV-infected, phytohemagglutinin (PHA)-stimulated peripheral lymphocytes which were harvested by sequential centrifugation (300×g for 7 minutes followed by 1500×g for 20 minutes), and were stored in liquid nitrogen. For binding studies, virus was concentrated from culture supernatants, harvested as above, by ultracentrifugation at 90,000×g for 90 minutes over a 15% cushion of Renograffin (E. R. Squibb) in 0.01 M Tris, 0.15 M NaCl, 1 mM EDTA, pH 8.0.

Anti-HTLV-III/LAV Reagents

Serum with high levels of antibody to HTLV-III/LAV was obtained from a homosexual man with chronic lymphadenopathy, and its specificity by immunofluorescence (46), Western blot analysis (47), and radioimmunoprecipitation (48) has been described. Portions of the IgG fraction were coupled with fluorescein isothiocyanate (FITC; FITC:protein ratio of 10.7 micrograms/ml), horseradish peroxidase (HPO; type VI; Sigma) and agarose as described (47, 49, 50, 51). Conjugates of IgG from a nonimmune serum were prepared in parallel.

Reverse Transcriptase Assay

Magnesium-dependent, particulate reverse transcriptase (RT) activity was measured with a template primer of $^{(A)}{}_n(dT)12$-18 (or $(dA)_n(dT)_{12-18}$ as the negative control) in the presence of 7.5 mM $Mg^{2+}$ (52).

Immunofluorescence Detection of Cytoplasmic AIDS Virus

Cultured cells ($1 \times 10^5$ in 0.1 ml) were centrifuged onto glass slides (Shandon Cytocentrifuge), fixed in 95% ethanol and 5% acetic acid at $-20°$ C. for 30 minutes, and rehydrated with three 10 minute changes of PBS (0.01 M $PO_4$, 0.15 M NaCl, pH 8.0). Slides were exposed to a $\frac{1}{500}$ dilution of FITC-anti-HTLV-III/LAV (19 micrograms/ml) for 30 minutes at room temperature. The slides were then washed (three changes, 10 minutes each) and mounted under a coverslip with 50% glycerol in PBS. The slides were examined with an epi-illuminated Leitz Orthoplan microscope at 630×power. Under these conditions, the FITC-anti-HTLV-III/LAV reagent is specific for HTLV-III/LAV. Uninfected PHA-stimulated cells, Epstein Barr (EB) virus-infected B cell lines, an adenovirus-infected cell line, several T cell lines, and HTLV-I and HTLV-II infected cell lines were not stained.

AIDS Virus Immunoassay (Antigen Capture Assay)

This is a sandwich immunoassay that has been described in detail (47). Briefly, culture supernatant is added to microtiter plate wells coated with anti-HTLV-III/LAV IgG. After the plates are washed, bound virus antigen is detected with HPO-anti-HTLV-III/LAV. This assay, which is at least as sensitive as the RT assay, is negative with culture supernatants from PHA-stimulated lymphocytes from numerous donors, EB virus-infected B cell lines, several T cell lines, polyclonal and cloned IL-2 dependent T cell lines, the myeloid line K562, as well as cell lines that harbor HTLV-I or HTLV-II. The cutoff $OD_{490}$ for discriminating a positive from a negative supernatant was determined in each run from the mean pius 2 SD of at least 10 replicative determinations on control (uninfected cell culture) supernatants harvested at the same time.

AIDS Virus Infectivity (ID-50) Assay

The microculture assay for the titration of infectious HTLV-III/LAV has been described in detail (47). Briefly, PHA-stimulated lymphocytes or cell lines ($2 \times 10^6$ cells/ml) are inoculated with serial 10-fold dilutions of virus inoculum and incubated for 18 hours at $37°$ C. The cells were then washed and plated in microculture (10 to 20 cultures per dilution:$1 \times 10^5$ cells per culture in 0.25 ml medium). Every 4 days, 100 microliters of supernatant was removed and replaced with fresh medium. Supernatants were then assayed for viral antigen by the antigen capture assay as described above. Infectious virus titer (ID-50) is defined as the reciprocal of the dilution at which 50% of the cultures are positive for virus (47).

VSV Pseudotype Assay

Vesicular stomatitis virus (VSV, Indiana strain, wild type) was propagated in cells producing the retrovirus required for the envelope pseudotype as described (53). Hyperimmune neutralizing sheep anti-VSV serum was added to the harvested VSV to inactivate non-pseudotype virions. The pseudotype titers ranged between $10^4$ and $10^5$ PFU/ml. For the assay, $2 \times 10^5$ cells to be infected with VSV pseudotypes were plated in 30 mm diameter tissue culture wells. HeLa, NIH 3T3, and L cells were naturally adherent; all other cells types were attached by pretreatment of the substratum with 50 micrograms/ml poly-L-lysine. After virus adsorption for 1 hour, the cells were washed and $10^6$ mink CCL64 or bovine MDBK cells were added to each well. These cells provide excellent plaques for secondary VSV infection but are resistant to infection by pseudotype virions. After allowing the plague indicator cells to settle and spread (approximately 90 minutes), the monolayers were overlaid with agar medium. VSV plaques were counted 2 days after infection. Anti-T4A monoclonal antibody (1:20), anti- HTLV-III serum (1:10), or anti-HTLV-I serum (1:10) were used to inhibit pseudotype plaque formation by pretreatment of cells 30 minutes before addition of pseudotypes as described by (54).

Syncytium Induction Assay $2\times10^5$ cells were co-cultivated with $2\times10^4$ H9 cells infected by and producing HTLV-III (55) in 10 mm diameter wells. The cultures were incubated at 37° C. and examined for syncytia formation after 18 hours as previously described (54, 56). Cells were five or more syncytia were scored as positive. Syncytium inhibition was assayed by adding anti-T4A monoclonal antibody (1:20) to the mixed cultures at the time of seeding.

Cytofluorometric Analysis and AIDS Virus Binding

The method has been described in detail (46). Briefly, cell surface T4 or T8 expression was detected by direct immunofluorescence with fluorescein-conjugated anti-T4A or anti-T8 monoclonal antibodies (OKT⁻4A, OKT⁻8). The diluent/wash buffer was 0.01 M $PO_4$, 0.15 M NaCl, pH 7.4, containing 0.1% bovine serum albumin, 2% v/v $AB^+$ human serum, and 0.01% $NaN_3$. All reagents were pretitered for optimal (saturating) binding. Cells ($5\times10^5$) were incubated in a 25 microliter dilution of monoclonal antibody for 30 minutes at 4° C. The cells were washed by centrifugation (300×g for 7 minutes), resuspended in 0.5 ml of 1% paraformaldehyde in saline, and analyzed with a fluorescence-activated cell sorter (FACS IV, Becton Dickinson). For HTLV-III/LAV binding, $5\times10^5$ cells were incubated with HTLV-III/LAV (500 ng in 10 microliters) for 30 minutes at 37° C. Washed cells were resuspended in 25 microliters of fluorescein-conjugated anti-HTLV-III/LAV for 30 minutes at 4° C. The cells were washed, resuspended in 1% paraformaldehyde, and analyzed by FACS as above. For inhibition of HTLV-III/LAV binding, cells were preincubated with anti-T4A or anti-T8 (20 ng in 20 microliters) for 30 minutes at 4° C. followed by addition of HTLV-III/LAV (500 ng in 10 microliters) for 30 minutes at 37° C. The cells were washed incubated with fluorescein-conjugated anti-HTLV-III/LAV, washed, resuspended in paraformaldehyde, and analyzed by FACS as above.

Cell Surface Radioiodination, Immunoprecipitation, and Gel Electrophoresis $T4^+$ NIH 3T3 transformants were surface radioiodinated by the lactoperoxidase technique (18) as follows: $4\times10^7$ cells were suspended in 1 ml of PBS containing 0.5 mM EDTA, 2 mCi $Na^{125}I$, and 20 micrograms lactoperoxidase. At times 0, 1, 5, 10, and 15 minutes, 10 microliters of 0.03% $H_2O_2$ were added. The reaction was carried out at 23° C. and was stopped at 20 minutes by 2 centrifugations in 50 volumes of cold PBS containing 10 mM NaI. Labeled cells were split into 4 tubes and incubated, as indicated, with HTLV-III/LAV (2 micrograms in 20 microliters) for 30 minutes at 37° C. Subsequent washes and manipulations were performed at 0° to 4° C. Washed cells were lysed by adding 1 ml of detergent lysing buffer (LB; 0.02 M Tris, 0.12 M NaCl, pH 8.0, containing 0.2 mM phenylethlsulfonylfluoride, 5 micrograms/ml aprotinin, 0.2 mM EGTA, 0.2 mM NaF, 0.2% sodium deoxycholate, and 0.5% (v/v) Nonidet P-40). Tubes were held on ice for 15 minutes, and nuclei were removed by centifugation at 3000×g for 20 minutes.

For absorptions, Sepharose conjugates of human anti-HTLV-III/LAV IgG, human nonimmune IgG, anti-T4A, and anti-T8 antiboboides were prepared as described (48). Lysates were preabsorbed with 200 microliters of Sepharose-nonimmune human IgG for 1.5 hours with rotation, and then immunoprecipitated with 20 microliters of Sepharose conjugates (as indicated) for 3 hours with rotation. Sepharose absorbants were washed 3 times: once with LB containing 0.5% NaCl; and once with LB containing 0.1% sodium dodecyl sulfate (SDS). Absorbed material was eluted at 65° C. for 30 minutes with 20 microliters of sample buffer (0.01 M Tris, pH 8.0, containing 2% SDS, 5% 2-mercapto-ethanol (v/v), 25 micropgrams bropphenol blue, and 10% glycerol (v/v). Electrophoresis was performed in a 3.3–20% gradient polyacrylamide gel with a #% stacking gel (57), and autoradiographs were formed by exposing the gel to Kodak XAR-5 film.

Virus Inhibition Assay $2\times10^5$ $T4^+$ JM T cells were exposed to AIDS virus at 0 minutes. The inhibitors ammonium chloride (20 mM) or amantadine (20 mM) were added at various times during the course of virus infection (0 minutes, 30 minutes, and 60 minutes). After 6 hours, cells were washed and replated in fresh medium (RPMI/I0%FCS). The effect of these agents on AIDS virus infection was determined 5 days post infection. The fraction of infected cells in the cultures expressing viral antigens was determined by immunofluorescence microscopy as described above (58).

RNA Isolation and Northern Blot Hybridizations

Total RNA was isolated from cells by homogenation in 4M guanidinium thiocyanate, followed by ultracentrifugation through a 5.7 M CsCl cushion (28). Poly(A)$^+$ selection was achieved by oligo(dT)-cellulose chromatography (Type 3, Collaborative Research) (29).

RNA was electrophoresed through a 1% agarose-formaldehyde gel (39) and transferred onto Hybond (Amersham). Northern blot hybridization was performed according to the procedures supplied by the manufacturer. Probes were nick-translated to a specific activity of 0.5-1× $10^9$ cpm/microgram with $\alpha^{32}P$-labeled deoxynucleotide triphosphates (59).

Results

Isolation of a T4 cDNA

The strategy used to isolate a T4 cDNA initially involved constructing L cell transformants that express T4 on their surface. cDNA synthesized from the mRNA of a $T4^+$ transformed fibroblast was enriched by subtractive hybridization and used as a probe to isolate a cDNA encoding T4 from a cDNA library made from the mRNA of peripheral T lymphocytes. The identity of $T4^+$ cDNA clones was determined by Northern and Southern blot analyses, and ultimately by the ability of these clones to transfer the $T4^+$ phenotype to recipient cells. Similar techniques have previously been employed to isolate the gene encoding the T8 protein (20).

Figure 1:
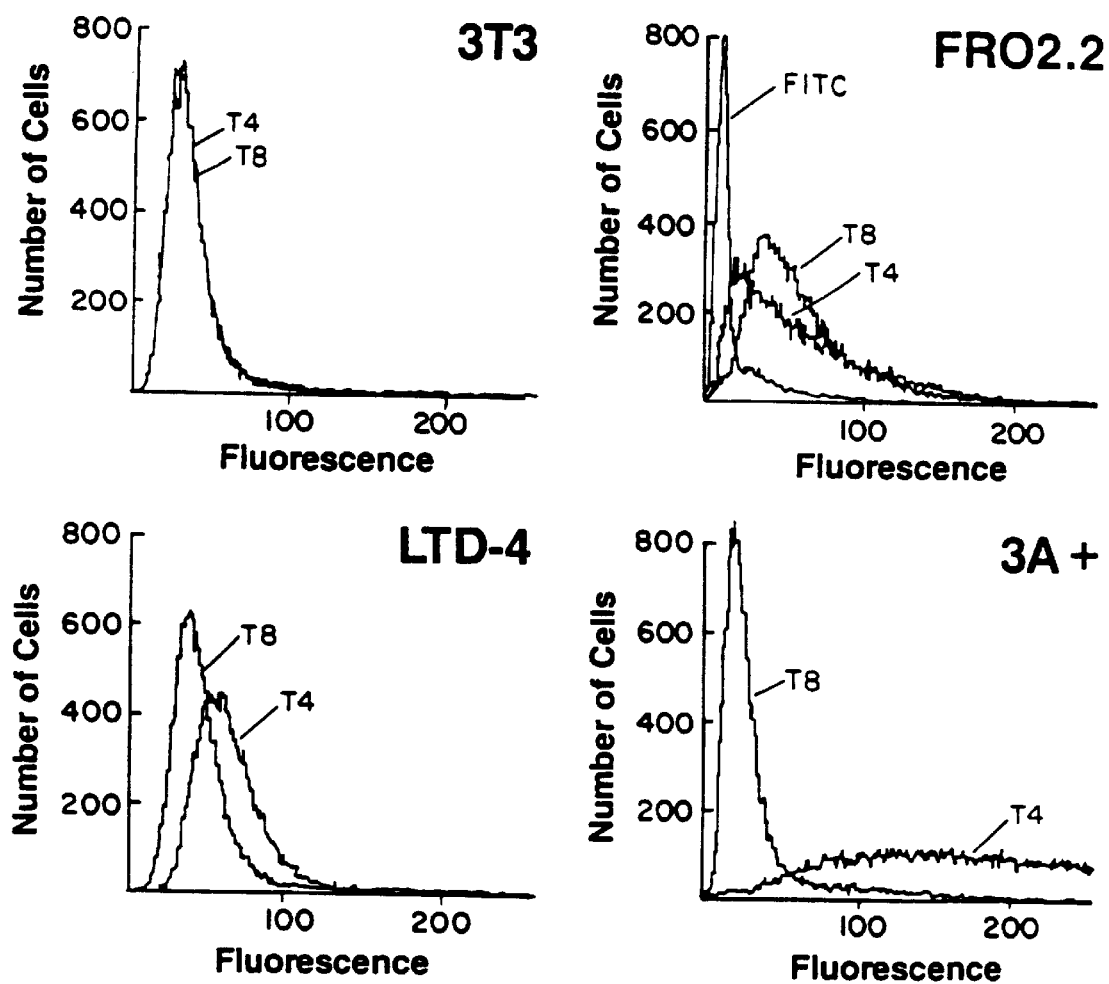
FIG. 1. Cytofluorographic Patterns of Indirect Immunofluorescent Staining with OKT‾4 and OKT‾8

Mouse L cells deficient in thymidine kinase (tk) were cotransformed with genomic DNA from the T cell leukemic cell line HUT-102 along with the tk-containing plasmid, pTK (25, 26). $tk^+$ L cell transformants expressing T cell surface proteins were identified by an in situ rosetting assay. $tk^+$ colonies were exposed to mouse monoclonal antibodies directed against T4 and were then incubated with red blood cells coupled with rabbit anti-mouse immunoglobulin. $T4^+$ transformants are visibly -red by virtue of their specific association with red blood cells. In this manner, one primary $T4^+$ transformant, LTD-4, was obtained. The expression of the T4 molecule by this clone was independently verified by cytofluorometric analysis (FIG. 1).

The mRNA population of the $T4^+$ transformant, LTD-4, should differ from that of an untransformed L cell only in the expression of newly transformed genes. These sequences were enriched for by annealing highly radioactive cDNA prepared from poly(A)$^+$ RNA of the $T4^+$ transformant with a vast excess of RNA from an untransformed L cell (32, 60).

cDNA incapable of hybridizing, even at high Rot values, was isolated by hydroxyapatite chromatography and used to screen a human peripheral T cell cDNA library constructed in the lambda cloning vector gt10. Four weakly hybridizing plaques were identified, plaque-purified and analyzed for the presence of T4 sequences.

To determine whether any of these clones encoded T4, Northern blot analyses were initially performed with RNA from T4+ and T4- peripheral T cells, leukemias, thymocytes, L cell transformants and nonlymphoid cells (FIG. 2). One of the four clones hybridized to an RNA present only in T4+ cells. This clone detects a 3 kb RNA present in the T4+ transformant, LTD-4, which is also present in a population of T4+ peripheral lymphocytes, a variety of T4+ leukemic cell lines, and thymocytes. No hybridization was observed with RNA from untransformed fibroblasts, T4- peripheral lymphocytes, HeLa cells, or human neuroblastoma cells.

The pattern of expression of RNA detected by this clone is consistent with the possibility that it encodes T4. However, this cDNA is only 0.6 kb in length but hybridizes to a 3 kb mRNA. Therefore, the human peripheral T cell cDNA library was rescreened and one clone (pT4B) was obtained which contained a 3 kb insert, close in size to that of the mature messenger RNA. Restriction maps of this clone are shown in FIGS. 3A and 3B.

Genomic Blot Analysis

Southern blot experiments (37) were next performed to demonstrate that the isolated cDNA clone hybridized with DNA from the T4+ transformant as well as human DNA, but not with untransformed mouse L cell DNA (FIG. 4). Genomic DNA from a variety of human cells reveals a set of five hybridizing fragments after cleavage with the enzyme BamHI. As expected, T4 sequences can be detected in the transformant LTD-4, but not in untransformed L cell DNA. The BamHI fragment closest to the 31 end of the gene (6.6 kb) is not present in LTD-4, presumably as a consequence of the integration event. Moreover, no gross rearrangements are apparent at this coarse level of analysis when comparing DNA from lymphoid and nonlymphoid cells. The sum of the molecular weights of the hybridizing fragments is 33 kb, suggesting that the T4 gene is quite large. A complete set of genomic clones spanning this region was obtained (see below) and the BamHI fragments were ordered by restriction analysis of these clones (FIG. 3A), confirming that the gene is large and must contain introns of significant lengths.

Expression of the T4 cDNA in Transformed Mouse Fibroblasts

Figure 3C:
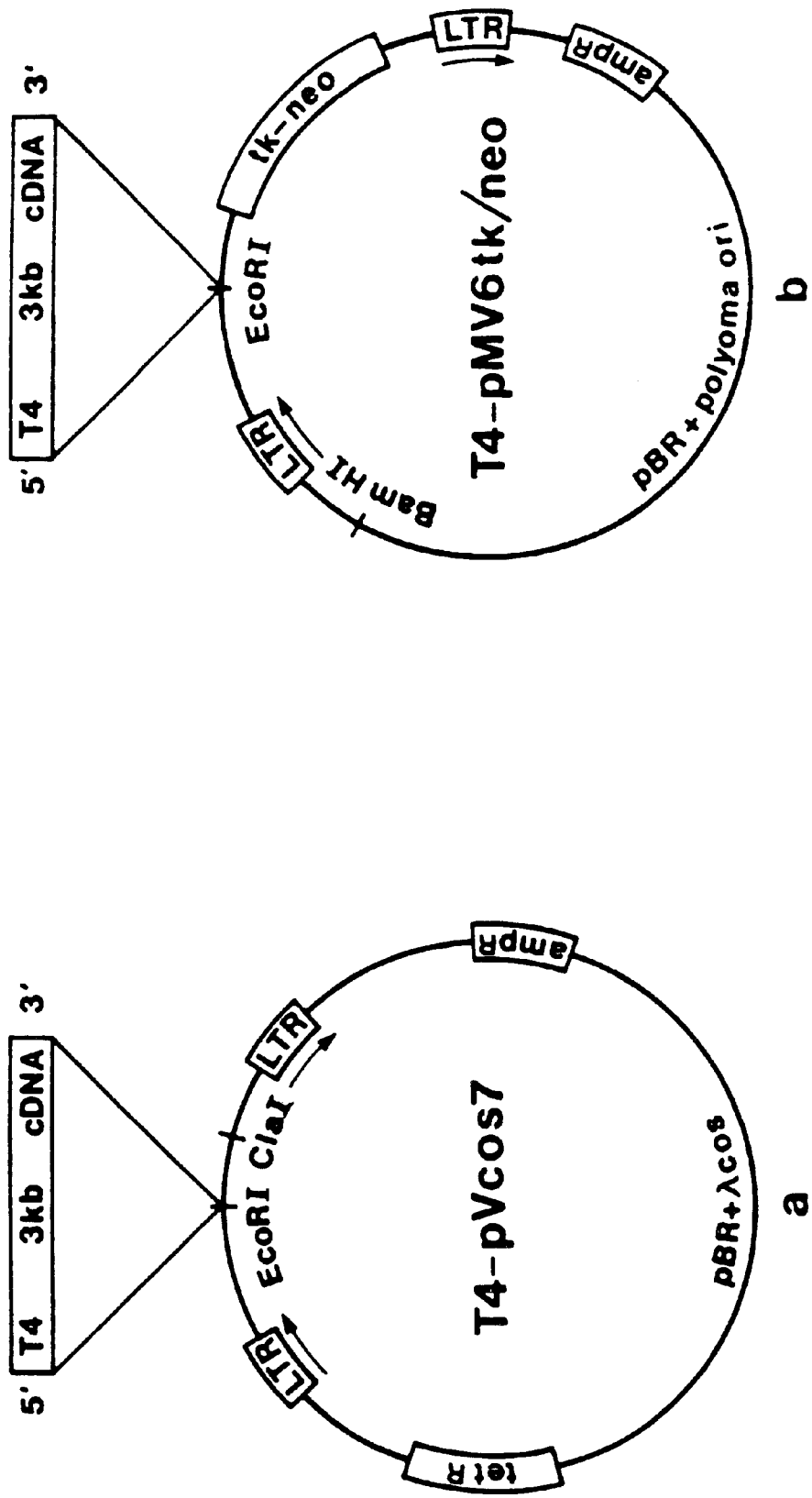

Further evidence that the isolated cDNA encodes T4 would be provided if this clone could convert fibroblasts to the T4+ phenotype after transformation. The T4 gene in chromosomal DNA is large and spans several genomic clones. Therefore, the cDNA clone was introduced into two retroviral expression vectors, pVcos7 and pMV6kt/neo, which contain the Moloney murine leukemia virus long terminal repeats (LTRs) flanking a single EcoRI cloning site (FIG. 3C). The 5'-LTR promotes transcription through the cloning site and the 3'-LTR contains sequences necessary for cleavage and polyadenylation. The vector pMV6tk/neo also contains the tk promoter fused to the coding region of the neomycin phosphotransferase gene. The construct employing pVcos7 requires transformation with an unlinked selectable marker, whereas pMV6tk/neo carries the neomycin resistance marker, which permits linked cotransformation. Neo+ colonies of NIH 3T3 cells obtained after transformation were selected by their ability to grow in media containing the neomycin analogue G418, and were screened using the resetting procedure to detect the expression of T4 on the cell surface. Approximately 50% of the G418 colonies obtained with pVcos7 and 75% of the colonies obtained with pMV6tk/neo were positive for T4 in this assay. Rosette-positive colonies were further analyzed by cytofluorometry to confirm that T4 is expressed on the transformed cell surface (FIG. 1).

Metabolic protein labeling experiments were performed which demonstrate that the T4+ transformed fibroblast and the T lymphocyte express a T4 protein of identical molecular weight. Untransformed NIH 3T3 cells, T4+ transformants and T lymphocytes were labeled for 12 hours in the presence of L-[$^{35}$S]-methionine (41). The cells were detergent solubilized and the lysate was passed over lentil lectin columns to enrich for glycoproteins (42). The bound glycoprotein fraction was eluted and immunoprecipitated with monoclonal antibodies directed against T4 (FIG. 5). Under reducing conditions, a glycoprotein migrating at a relative molecular mass of 55 kd is detected in extracts from T lymphocytes and two independent T4+ transformants.

This protein is not detected in control 3T3 fibroblasts. Under nonreducing conditions, a 51 kd glycoprotein is immunoprecipitated with anti-T4 in T cells and in the transformed fibroblasts.

These experiments demonstrate that the transformants express a 55 kd glycoprotein immunoprecipitated with anti-T4 which is identical in size to that expressed on the surface of T lymphocytes. Thus, Northern and Southern analyses using the isolated cDNA, taken together with the ability of this cDNA to confer the T4+ phenotype to mouse fibroblasts, indicate that the entire coding sequence of the T cell surface protein T4 had been cloned.

Nucleotide Sequence of the T4 cDNA and the Deduced Protein Sequence

Figure 7:
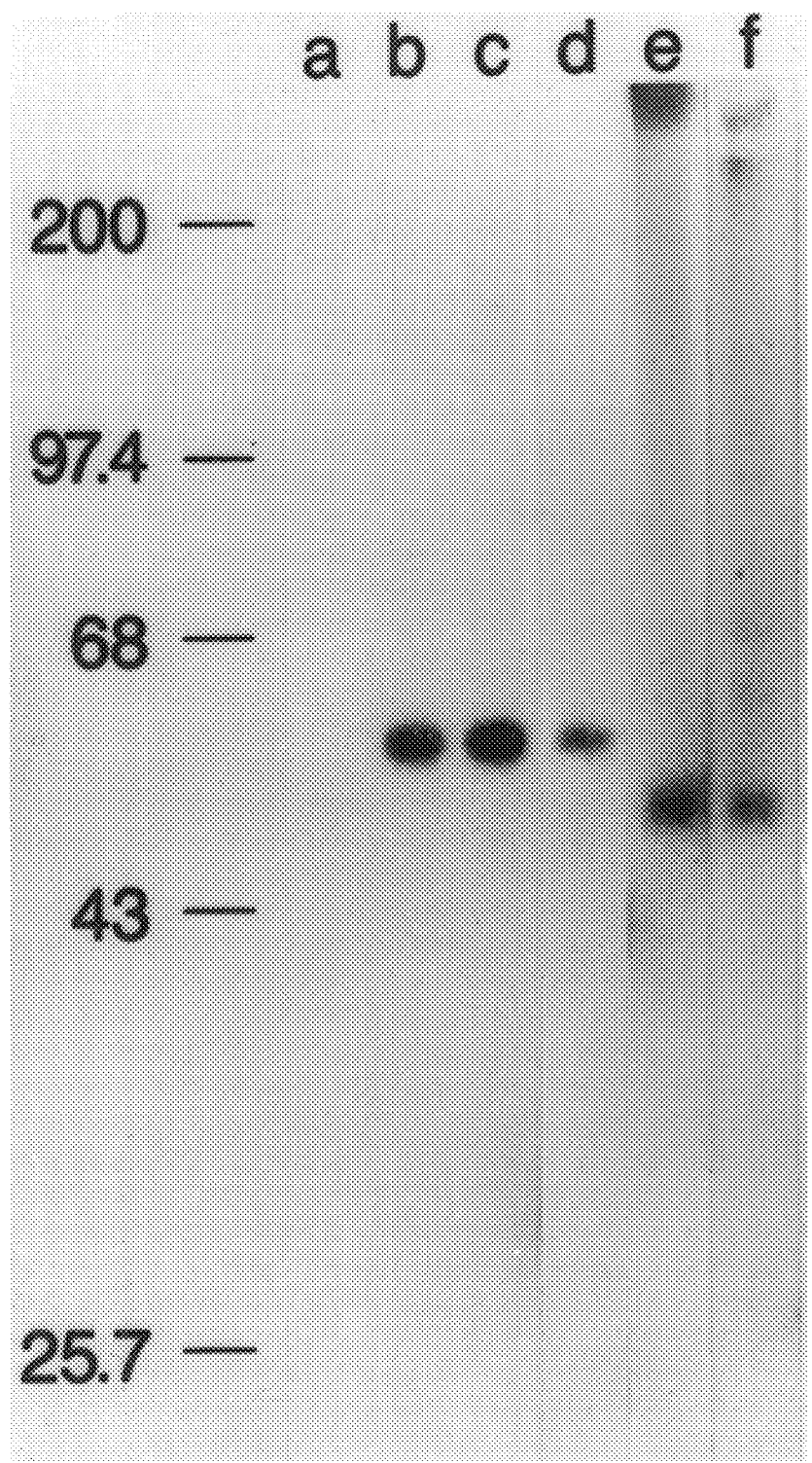

The complete nucleotide sequence of the T4 coding region was determined by sequencing both strands of the 3 kb cDNA insert using the dideoxy termination method (35, 36). The complete nucleotide sequence and the predicted protein sequence are shown in FIG. 6. The longest open reading frame begins at position 76 with a methionine codon surrounded by the initiation consensus sequence PurNNAT-GPur (61). This reading frame extends 1374 nucleotides, encoding a polypeptide containing 458 amino acids. The contiguity of this reading frame was confirmed by inserting this cDNA into the RNA expression vector pSP6 (40). RNA synthesized from this vector, when translated in vitro, directs the synthesis of an unmodified 51 kd protein, the precise molecular weight predicted from the nucleotide sequence (FIG. 7).

T4 is comprised of a leader sequence, four tandem variable-joining (VJ)-like regions, and a membrane-spanning domain each sharing homology with corresponding regions of different members of the immunoglobulin gene family (62, 63) (FIGS. 6 and 8). A stretch of hydrophobic residues, corresponding to a leader peptide predicted by a Kyte-Dolittle (64) hydropathicity plot, immediately follows the initiation codon. Although the exact position at which the native T4 protein is processed cannot be determined, it is contemplated that cleavage occurs just after the threonine at positions -1 based on known cleavage patterns (65). Therefore, the signal peptide contains 23 amino acids and the processed T4 protein consists of 435 residues.

Figure 9A:
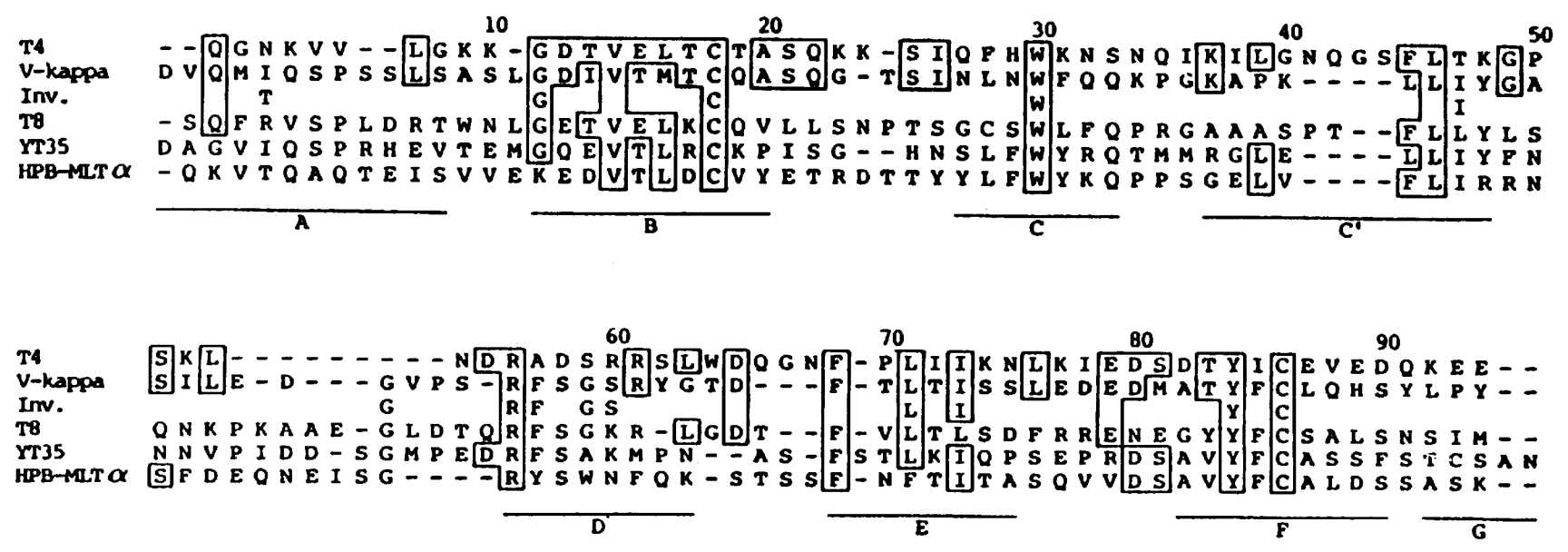

Residues 1–94 of the mature protein share both amino acid and structural homology with the immunogloblin light chain variable domain (FIG. 9A). The overall homology of this domain with immunoglobulin variable regions is 32%. Sequence comparison between the V-regions of light chain immunoglobulins and the N-terminal V-like region (V1) of T4 demonstrates that eight out of 14 invariant residues are conserved (66). This domain contains two cysteine residues, separated by 67 amino acids, whose positions and spacing are analogous to that found in light chain immunoglobulins and related molecules (67). These cysteines may be capable of forming the conserved intrastrand disulfide bond characteristic of V domains. This suggestion is supported by our observation that T4 migrates more rapidly under nonreducing conditions than under reducing conditions, consistent with the formation of at least one intrastrand linkage (FIG. 5, lanes e and f).

Aside from homologies at the level of individual amino acids, the VI domain of T4 shares structural features with immunoglobulin variable regions. Immunoglobul in variable and constant domains told in a characteristic pattern in which a series of antiparallel β-strands fold to rorm two β-sheets (67, 68). These β-sheets are held togetner both by a disulphide bridge and by characteristic hydrophobic interactions. To determine how tne predicted secondary structure of the V-like domain of T4 compares with the structure of the V domains of lignt chain immunoglobulins, two-dimensional structural alignments were performed. Also, a plot of probable β-strands and β-turns in these sequences using the empirically derived algorithm of Chou and Fasman. (69) was obtained. These analyses suggest the presence of seven β-strands within the V-like domain of T4 which closely match those found in the immunoglobulin V domain (FIG. 9A). The two conserved cysteines of T4 are found within β-strands B and F, matching exactly the positions of the cysteines in the V region known to form the conserved disulphide bond in immunoglobul in. A tryptophan residue lies 12 amino acids downstream of the first cysteine and a tyrosine residue is situated two amino acids before the second cysteine. These residues are highly characteristic or β-strands C and F, respectively in light chain V regions. In addition, an aspartate residue is found six amino acids before the second cysteine, and an arginine residue lies at the base of β-strand D. These charged residues are highly characteristic of V domains (67). Finally, patches of alternating hydrophobic residues are present throughout the β-strands, which strengthen the interaction of the two β-sheets.

Figure 9B:
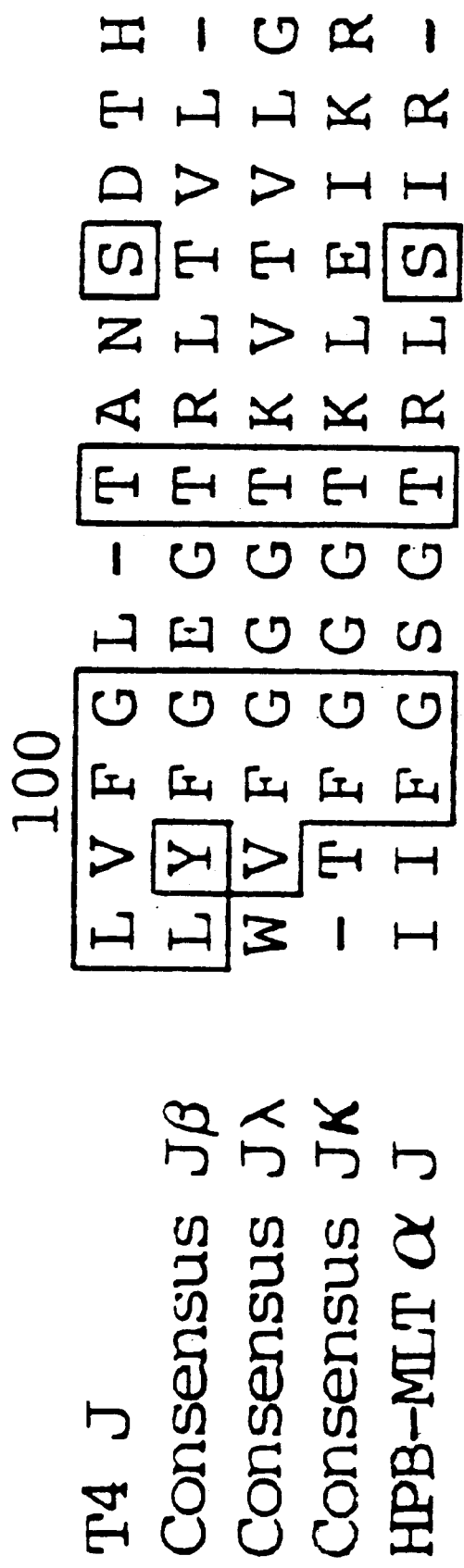

The V1 domain of T4 is followed by a stretch of amino acid residues bearing significant homology to the joining (J)regions of immunoglobulins and T cell antigen receptors. In FIG. 9B, this J-like region of T4 is aligned with the consensus joining sequences of immunoglobulin light chains and the two chains of the T cell antigen receptor. This J-like region is followed by a 265 amino acid stretch which may be structurally divided into three additional VJ-like domains with statistically significant sequence and structural homology to prototype immunoglobulin VJ regions (FIGS. 6 and 8). Additionally, this sequence contains two potential N-linked glycosylation sites (Asn-Leu-Thr; FIG. 6).

The extracellular domain is followed by a putative transmembrane sequence, predicted by a hydropathicity plot (64), which contains only hydrophobic and neutral amino acid residues. This segment bears striking homology to the transmembrane exon of the β-chains of class II major histocompatibility proteins (FIG. 9C). Alignment of the transmembrane regions of T4 and MHC class II β-chains reveals 48% homology without gaps. Following the membrane-spanning segment, a highly charged sequence of 40 amino acids comprise the cytoplasmic domain (FIGS. 6 and 8).

The T4 Gene: Chromosomal Location and Intron-Exon Positions

The T4 cDNA was used to determine the chromosomal location of the T4 gene by analyzing its segregation pattern in a panel of mouse-human somatic cell hybrids and by in situ hybridization to human metaphase chromosomes (101). Genomic blot experiments and in situ hybridization indicate that the T4 gene resides on the short arm of human chromosome 12, between regions 12p12 and 12pter.

A set of overlapping genomic clones spanning the T4 gene was obtained by screening human genomic libraries constructed in the lambda cloning vectors Charon 4 and EMLB-3 (31) with a radiolabeled pT4B cDNA insert (70). Characterization of these clones by both restriction and Southern blot analyses indicated that they contained the entire T4 coding sequence. The complete intron-exon organization of the T4 gene was then determined by sequencing specific fragments of the genomic clones using the dideoxy termination procedure (35, 36).

The T4 gene is comprised of 9 exons split by 8 introns as shown in FIGS. 8 and 10. The first exon contains the 5'-untranslated region and the leader segment. The first variable-like domain, $V_1$, is split by a large intron located at nucleotide position 289 (FIG. 6). Therefore, the $V_1J_1$ domain is encoded by the second and third exons and the $V_2J_2$, $V_3J_3$, $V_4J_4$, and transmembrane (TM) domains are each encoded by separate exons (exons 4-7). The cytoplasmic domain (CYT) is split by an intron and the last portion of the cytoplasmic domain and the 3'-untranslated region are encoded by the ninth exon.

The Construction of T4$^+$ and T8$^+$ Transformed Cells

The experimental approach used to study the role of T4 in AIDS virus infection initially involved the introduction of the T4 gene into T4$^-$ cell lines incapable of supporting viral infection. The transformed cells were then tested for susceptibility to AIDS virus, followed by studies on the mechanism by which T4 mediates viral infection.

A full length cDNA clone encoding the surface protein T4 was subcloned into the retroviral expression vector, pMV7. The expression vector, pMV7 (FIG. 11A), contains two directly repeated Moloney murine sarcoma virus long terminal repeats (LTRs) which flank a single EcORI cloning site. The 5'-LTR constitutively promotes transcription through the cloning site, whereas the 3'-LTR provides sequences necessary for cleavage and polyadenylation of the RNA. In addition, pMV7 contains the herpesvirus thymidine kinase promoter (tk) fused to the coding region of the bacterial neomycin phosphotransferase gene (neo), a dominant selectable marker, permitting linked cotransformation and infection.

T4-pMV7 was introduced into Ψ-2 and Ψ-AM cells, NIH 3T3 cell lines containing defective ecotropic and amphotropic proviruses, respectively (FIG. 11B) (44, 59). Both cell lines are incapable of encapsidating endogenous viral RNA but can provide all obligate trans viral functions. Stable transfection of these cell lines with T4-pMV7 results in the production of recombinant retroviral stocks encoding T4 which are free of helper virus. These pure viral stocks can then be used to efficiently introduce T4 sequences into both mouse and human cells without the production of retrovirus by the target cell.

Briefly, T4-pMV7 DNA was introduced into Ψ-2 cells using the procedure of DNA-mediated gene transfer (FIG. 11B) (25, 27). Neo$^+$ positive colonies were selected by their ability to grow in media containing the neomycin analog G418 (Geneticin*) and screened for the expression of T4 on the cell surface using an in situ rosetting assay (20, 70).

Figure 11B:
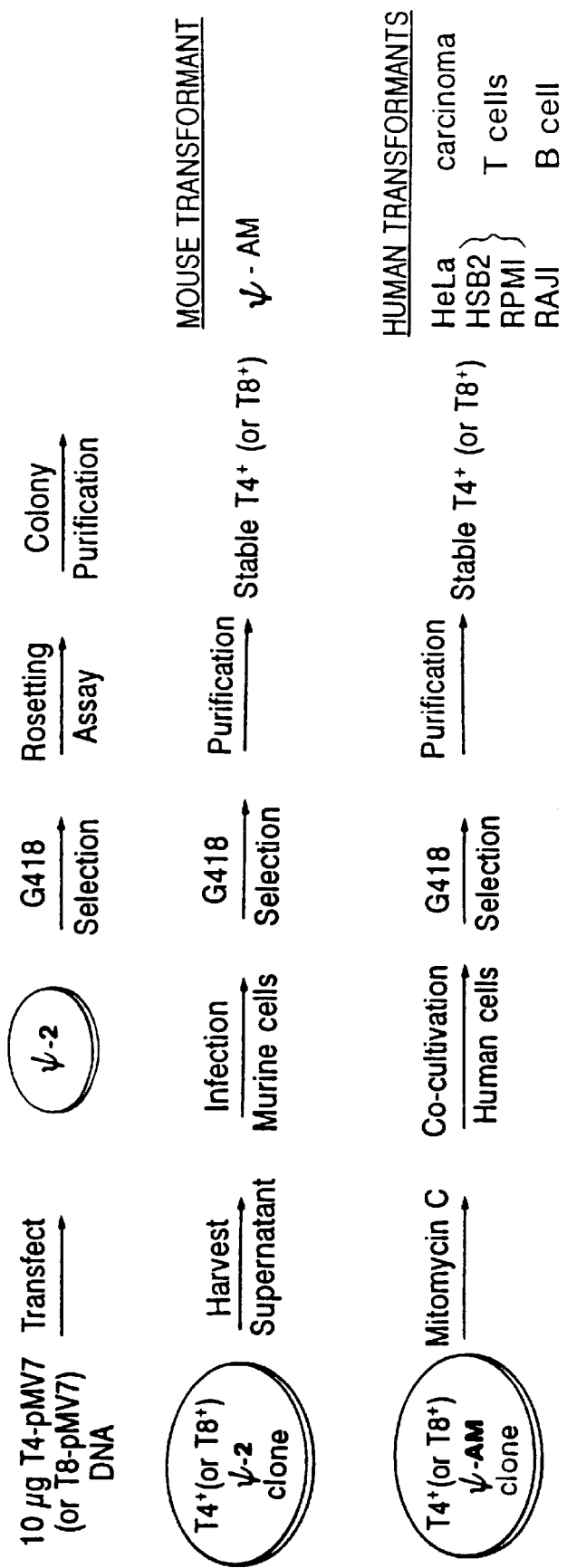

Colonies of transfected Ψ-2 cells expressing T4 were then identified which produce recombinant retrovirus in titers of $10^5$ cfu/ml. $T4^+$ Ψ-2 clones were then used to generate retroviruses capable of infecting mouse Ψ-AM cells. T4 expressing Ψ-AM clones were isolated which yield recombinant retroviral titers of $10^4$ cfu/ml. $T4^+$ human transformants were generated by co-cultivation of cells with mitomycin-C treated or Ψ-AM clones (FIG. 11B). $T4^+$ transformants were subsequently analyzed by Northern blot analysis and flow cytometry to confirm that T4 is expressed and is present on the cell surface. Control cell lines expressing the surface protein T8 were constructed in an analogous manner.

T4 is Essential for AIDS Virus Infection

To initially determine whether the presence of the T4 protein on the surface of a human lymphocyte is sufficient to render the cell susceptible to AIDS virus infection, transformants of the primitive T cell leukemic line, HSB2 (71), which expresses only the early T lymphocyte proteins Tl and Tll on its surface, were constructed. HSB2 expresses neither T4 nor T8, nor does it express the T cell antigen receptor or the associated complex of T3 proteins. Transformants of HSB2 which express either the T4 or T8 proteins on the cell surface were selected and used to determine the susceptibility of these cell lines to AIDS virus infection. Several different experimental approaches were employed to assess AIDS virus infection, including expression of reverse transcriptase (52), expression of virus in the cytoplasm of the cell by immunofluorescence microscopy (46), detection of viral antigens in the culture supernatant using an immunoassay (47), as well as production of infectious virions by supernate subculture with phytohemagglutinin (PHA)-stimulated peripheral lymphocytes (46). Using these assays, evidence of AIDS virus infection of the HSB2 cell line was not observed (Table I).

infected with AIDS virus are superinfected with VSV, a proportion of the progeny VSV assemble sufficient AIDS virus envelope glycoprotein to resist neutralization by hyperimmune anti-VSV serum. The host range of these VSV (AIDS) pseudotype virions is restricted to cells expressing receptors specific to the AIDS virus. Following penetration of the cell and uncoating of the virion, the transcapsidated VSV genome replicates to produce non-pseudotype particles. During the secondary infection, progeny VSV released from infected cells penetrate and destroy neighboring indicator cells resistant to VSV (AIDS) pseudotype infection (mink CCL64 or bovine MDBK cells), resulting in the formation of VSV plaques which are then scored. Thus, infection with VSV (AIDS) pseudotypes provides a quantitiative cytopathic plaque assay for viral entry (54). In this assay, no plaques over background were observed when HSB2 cells were exposed to VSV (AIDS) pseudotypes (Table I). In control experiments with pseudotypes of VSV RNA encapsidated in an HTLV-I envelope (VSV (HTLV-I)), numerous plaques were observed, demonstrating that the HSB2 cell, which bears HTLV-I receptors, is capable of replicating VSV efficiently. These observations demonstrate that the VSV genome encapsidated in an AIDS virus envelope is incapable of entering HSB2 cells.

Whether the introduction of a functional T4 cDNA into HSB2 would render this cell susceptible to AIDS virus infection was next studied (Table I). Exposure of HSB2-$T4^+$ transformants to AIDS virus results in a productive viral infection as determined by expression of reverse transcriptase activity (52), expression of virus in the cytoplasm of the cell by immunofluorescence microscopy (46), detection of viral antigen in the culture supernatant using an immunoassay (47), as well as the production of infectious virus by supernate subculture with PHA-stimulated lymphocytes (Table I) (46). Control HSB2-$T8^+$ cells were consistently negative in each of the assays.

TABLE I

Susceptibility of $T4^+$ and $T8^+$ Human Transformants to AIDS Virus Infection

| HUMAN CELL | Maximum Reverse Transcriptase | Cytoplasmic Virus | Supernate Viral Ag | Supernate Subculture | Syncytium Induction | VSV (AIDS) Pseudotype Infection | Virus Binding |
|---|---|---|---|---|---|---|---|
| CEM ($T4^+$) | 675023 | + | + | + | + | + | + |
| HSB2 | 4245 | − | − | − | − | − | − |
| HSB2-$T8^+$ | 4460 | − | − | − | − | − | − |
| HSB2-$T4^+$ | 190915 | + | + | + | + | + | + |
| Raji | ND | ND | ND | ND | − | − | ND |
| Raji-$T8^+$ | 5595 | − | − | − | − | − | − |
| Raji-$T4^+$ | 103500 | + | + | + | + | + | + |
| HeLa | 6438 | − | − | − | − | − | − |
| HeLa-$T8^+$ | 4875 | − | − | − | − | ND | − |
| HeLa-$T4^+$ | 48125 | + | + | + | + | + | + |

$5 \times 10^6$ cells were inoculated with AIDS virus, incubated at 37° C. for 24 hours, washed, and replated in fresh media. Cells and supernatants were removed at days 3, 6, 9, 12, 16, 20, 24, and 28 and used in four virus detection assays: reverse transcriptase, cytoplasmic virus, supernate viral antigen, and supernate subculture.
The results of the pseudotype infection experiments are expressed as follows: + ($\geq 10^3$ PFU/ml); − (10 PFU/ml); ND, not determined.

In addition, it has been previously demonstrated that extensive cell fusion occurs when uninfected human cells bearing receptors for AIDS virus are co-cultivated with cells producing AIDS virus (54). In this assay, there is no induction of syncytia when HSB2 cells are mixed with AIDS virus-producing H9 cells (Table I), although abundant syncytia are formed with HTLV-I and HTLV-II producing cells (data not shown).

Finally, viral entry was tested for using pseudotypes of vesicular stomatitis virus (VSV) bearing the envelope glycoproteins of the AIDS virus (Table I) (53, 54). When cells In addition, the efficiency with which different $T4^+$ T cells are infected with AIDS virus was also examined. HSB2-$T4^+$ and HSB2-$T8^+$ transformants, the naturally-isolated $T4^+$ T cell line CEM, as well as PHA-stimulated peripheral lymphocytes were exposed to serial 10-fold dilutions of AIDS virus, washed, and plated in microculture. The frequency of infected cultures was then determined using an immunoassay 12 days after exposure to virus (FIG. 12) (47). In this manner, the titer of AIDS virus required to infect 50% of the exposed cultures (ID-50) was defined. The ID-50 of PHA-stimulated peripheral lymphocytes is 2-3 orders of magnitude greater than that observed for either naturally-isolated or transformed T4+ cell lines. The efficiency of infection of HSB2-T4+ cells is about 10 fold higher than that observed for the naturally-isolated T4+ T cell line CEM (FIG. 12). Control HSB2-T8+ cells are not susceptible to infection even at the highest virus titers examined.

The ability of HSB2-T4+ cells to support both syncytia formation and the replication of VSV (AIDS) pseudotypes was also studied. When HSB2-T4+ cells are co-cultivated with AIDS virus producing H9 cells, syncytia formation is readily observed within 18 hours (Tables I and II). Moreover, syncytium induction is abolished by pretreating cultures with anti-T4A monoclonal antibody (Table II). Finally, when HSB2-T4+ cells are exposed to VSV (AIDS) pseudotypes, infectious VSV particles are produced which destroy neighboring indicator cells (Tables I and III). Furthermore, plaque formation is inhibited by pretreatment with either anti-AIDS virus antibody or anti-T4A monoclonal antibody (Table III). Control HSB2-T8+ cells are consistently negative in each of the seven assays employed to detect AIDS virus infection (Tables I, II, and III). These observations provide genetic evidence that in an immature human T lymphocyte, the mere presence of the T4 protein provides an essential function required for AIDS virus infection.

TABLE II

Induction of Syncytia in T4+ Human Transformants

| HUMAN CELLS | SYNCYTIUM INDUCTION | |
|---|---|---|
| | H9/AIDS | H9/AIDS + αT4A |
| JM(T4+) | +++++ | – |
| 8166 (T4+) | +++++ | – |
| HSB2 | – | ND |
| HSB2-T8+ | – | ND |
| HSB2-T4+ | ++ | – |
| Raji | – | ND |
| Raji-T8+ | – | ND |
| Raji-T4+ | +++ | – |
| HeLa | – | ND |
| HeLa-T8+ | – | ND |
| HeLa-T4+ | +++++ | – |

$2 \times 10^5$ cells were co-cultivated with $2 \times 10^4$ AIDS virus-producing H9 cells (H9/AIDS) and incubated at 37° C. The cultures were examined for syncytia formation after 18 hours. The results are expressed as the approximate percentage of nuclei contained within syncytia: – (no syncytia); ++ (25%); +++ (50%) +++++(90%); ND (not determined). Syncytium inhibition was assayed by adding anti-T4A monoclonal antibody (αT4A; 1:20) to the mixed cultures at the time of seeding. The natuarlly-isolated T4+ T cell lines JM and 8166 served as positive controls in these studies.

TABLE III

VSV Pseudotype Cytopathic Plaque Assay on T4+ and T8+ Human Transformants

| HUMAN CELLS | VSV (HTLV-I) | + αHTLV-I | VSV (AIDS) | + αAIDS | + αT4A |
|---|---|---|---|---|---|
| CEM (T4+) | 20,000 | 50 | 42,000 | 50 | 200 |
| HSB2-T8+ | 10,000 | 50 | 0 | ND | ND |
| HSB2-T4+ | 12,000 | 50 | 1,000 | 100 | 300 |
| Raji-T8+ | 5,000 | ND | 0 | ND | ND |
| Raji-T4+ | 5,000 | 50 | 1,500 | 25 | 150 |
| HeLa | 10,000 | ND | 0 | ND | ND |
| HeLa-T4+ | 10,000 | 50 | 17,000 | 50 | 200 |

$2 \times 10^5$ cells were incubated with VSV (AIDS) pseudotypes (53, 54) for 1 hour at 37° C. The cells were then washed and $1 \times 10^6$ mink CCL64 or bovine MDBK plaque indicator cells, permissive to VSV infection but resistant to VSV (AIDS), were added to each well. The cultures were then overlaid with agar medium and scored for VSV plaques two days post infection. Anti-T4A monoclonal antibody (α4A; 1:20) or anti-AIDS virus serum (αAIDS; 1:10) were used to inhibit VSV (AIDS) pseudotype plaque formation be pretreatment of cells 30 minutes before exposure to pseudotypes (54). VSV (HTLV-I) pseudotypes, which plate on a wide variety of human cell types (54), were used as controls in these experiments. Anti-HTLV-I serum (1:10) was used to block VSV (HTLV-I) pseudotype plaque formation. The results are expressed as PFU/ml; ND (not determined).

AIDS Virus Infection Is Not Restricted to T Lymphocytes

A functional T4 cDNA was introduced into two human non-T cell lines: HeLa, an epithelial cell line derived from a cervical carcinoma (72), and Raji, a B lymphoblastoid cell line derived from a patient with Burkitt's lymphoma (73) (FIG. 11B). Prior to retrovirus-mediated gene transfer, these cell lines do not express surface T4 protein or T4 mRNA, nor are they susceptible to AIDS virus infection (Table I). In addition, the parental cell lines do not support the induction of syncytium nor the plating of VSV (AIDS) pseudotypes (Tables I, II and III).

In contrast, T4+ Raji and HeLa transformants support AIDS virus infection by all of the criteria previously described (Table I). The efficiency with which Raji-T4+ cells can be infected with AIDS virus approximates that of HSB2-T4+ cells and is about 10 fold higher than the efficiency of infection of the naturally-isolated T4+ T cell line CEM (FIG. 12). Moreover, upon co-cultivation with AIDS virus-producing H9 cells, Raji-T4+ and HeLa-T4+ cells support the induction of syncytia which is abolished by pretreating cultures with anti-T4A monoclonal antibody (Tables I and II; FIG. 13). In addition, exposure of these cells to VSV (AIDS) pseudotypes results in the production of infectious VSV and the formation of plaques which are inhibited by pretreatment with anti-AIDS virus antibody or anti-T4A monoclonal antibody (Tables I and III). Control Raji-T8+ and HeLa-T8+ transformants are consistently negative in each of these assays (Tables I, II, and III).

Therefore, the introduction of a functional T4 gene into either human T lymphocytes, B lymphocytes, or epithelial cells is sufficient to render such cells susceptible to AIDS virus infection. Taken together, these observations indicate that the T4+ T cell tropism observed in vivo is a consequence of the restricted expression of the T4 molecule and not the nature of the cell type in which it is expressed.

AIDS Virus Binds to Surface T4 Protein

The previous experiments provide genetic evidence that T4 expression is required for AIDS virus infection but do not provide information on the role of this molecule in the viral life cycle. The observation that surface expression of T4 is necessary for AIDS virus infection suggests that T4 is the AIDS virus receptor. Cytofluorometry was therefore used to examine the binding of AIDS virus to the surfaces of T4$^+$ and T8$^+$ transformed human cells (Table I; FIG. 14). HSB2, Raji, and HeLa cells, and the T4$^+$ or T8$^+$ transformants, were incubated with AIDS virus. Following viral absorption, the cells were washed, exposed to fluorescein-conjugated anti-AIDS virus antibody, and analyzed by flow cytometry. This assay indicated that the AIDS virus binds efficiently and specifically to the human transformants expressing surface T4, but not to the T4$^-$ parental cells nor to the T8$^+$ transformants (FIG. 14, column B; Table I). The binding of AIDS virus to the T4$^+$ cells is abolished by preincubation with anti-T4A monoclonal antibody but not by preincubation with anti-T8 monoclonal antibody (FIG. 14, column C). Moreover, when T4$^+$ transformed cells are exposed to AIDS virus, the T4 glycoprotein coprecipitates with the viral envelope glycoprotein, suggesting a direct physical association between these molecules (data not shown). These results indicate that the AIDS virus binds to the T4 molecule on the cell surface and that this binding is independent of other T cell-specific proteins since binding occurs to all T4$^+$ cell types examined.

Previous studies have described two distinct pathways of entry for enveloped viruses (74, 75, 76, 77). Some viruses fuse directly with the plasma membrane, releasing their nucleocapsids into the cytoplasm, whereas others are internalized by receptor-mediated endocytosis. The acidic environment of the endosome then facilitates fusion of the viral envelope with the limiting membrane of the vacuole. Infection by viruses which enter cells via the endocytic pathway can be inhibited by treating cells with agents such as weak bases which deacidify the endosome (58, 78, 79, 80). In the presence of ammonium chloride, fusion is blocked in the endosome but lysosomal degradation still proceeds at a reduced rate (80).

The effect of ammonium chloride on AIDS virus infection of the T4$^+$ T cell line JM was therefore examined. In the absence of ammonium chloride, over 50% of JM cells exposed to AIDS virus express viral antigens five days after infection as determined by immunofluorescence microscopy. If JM cells are exposed to ammonium chloride (for 6 hours) either at the time of addition of virus or within 30 minutes after the addition of virus, greater than 95% inhibition of viral infection was observed. However, if cells were treated with ammonium chloride one hour after the addition of virus, no inhibition of infection was observed, a finding consistent with the kinetics of viral entry described for other viruses which enter cells via receptor-mediated endocytosis. Finally, the ammonium chloride effect was completely reversible. Cells exposed to ammonium chloride for one hour, and then washed free of the compound and exposed to AIDS virus, supported control levels of viral infection. These results are consistent with previous observations that upon removal of ammonium chloride, the pH of the endosome returns to the original low values within 1–2 minutes (78, 80). Similar results with amantadine, a compound which deacidifies the endosome, were obtained.

These results are consistent with a mechanism of viral entry which involves endocytosis of the T4-AIDS virus complex and low pH-induced fusion of the viral envelope with the limiting membrane of the endosome, releasing the viral nucleocapsid into the cytoplasm of the cell.

T4 mRNA is Expressed in the Brain

Figure 15A:
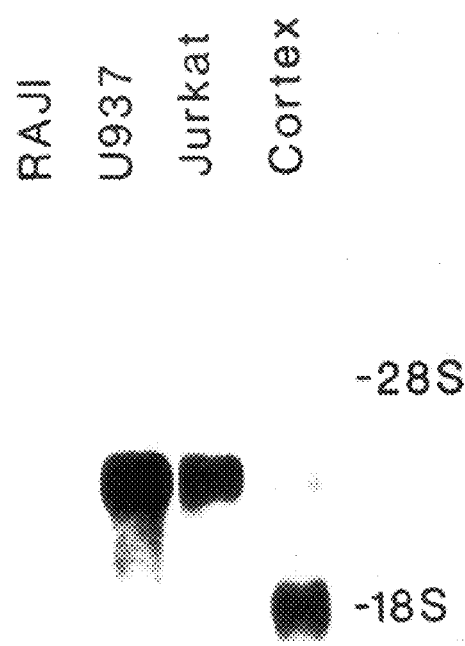

In addition to the disruption of the cellular immune system, AIDS is frequently accompanied by central nervous system (CNS) disorders which are thought to be the consequence of the direct infection of brain cells by the AIDS virus (81). It was therefore of interest to determine whether T4 is expressed in cells within the CNS, thereby providing an explanation for the neurotropic properties of the virus. Northern blot analyses of RNA prepared from both human and mouse brains were performed to determine whether T4 mRNA sequences are expressed in the CNS (FIG. 15). Poly(A)$^+$ RNA derived from human cerebral cortex contains two distinct T4 mRNAs with molecular weights of approximately 3 and 1.8 kb (FIG. 15A). The weaker 3 kb RNA is identical in size to the mRNA expressed by two T4$^+$ leukemic cell lines, U937 (monocytic cell line) and Jurkat (T cell line), as well as by Peripheral T lymphocytes. The smaller, more abundant 1.8 kb mRNA absent from T lymphocytes could result from alternative splicing or alternative 5' or 3' termini.

Figure 15B:
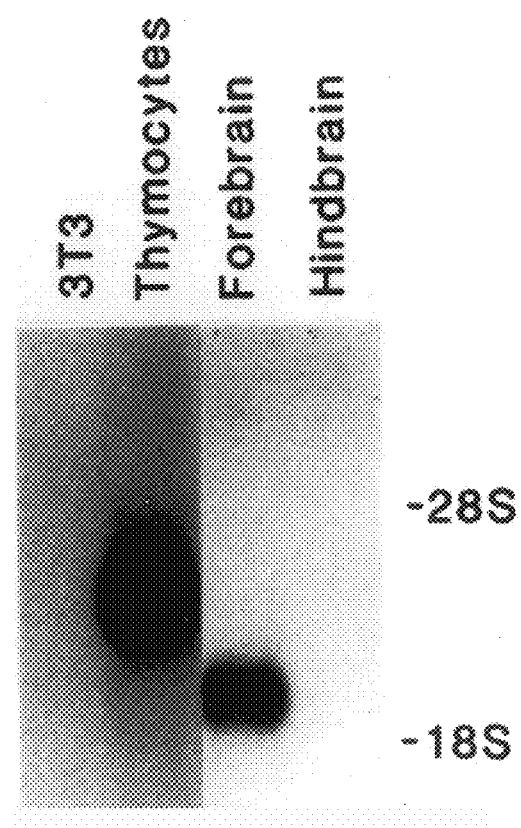

A more careful analysis of the localization of T4 mRNA was performed by isolating Poly(A)$^+$ RNA from specific regions of the mouse brain (FIG. 15B). Hybridization with radiolabeled cDNA encoding the homologue of T4, L3T4, reveals an intense 2.2 kb mRNA in mouse forebrain which is absent from hindbrain samples. The 2.2 kb L3T4 mRNA is detectable in the cortex, hypothalamus, and is most abundant in the striatum, but is absent from the cerebellum, brain stem, or spinal cord (data not shown). This 2.2 kb mRNA detected in the CNS is approximately 1 kb smaller than the 3.2 kb mRNA encoding L3T4 in thymocytes (FIG. 15B). These results indicate that the neurotropism displayed by the AIDs virus is likely to be the result of surface expression of the T4 molecule on brain cells. The level of mRNA detected in forebrain is about ⅓₀th the level in thymocytes. This may reflect low level expression by a large number of cells or higher levels of expression by a small subpopulation of cells. It is not known at present whether T4 is expressed by neurons or supporting cells. The presence of a variant transcript in the CNS, however, makes it unlikely that the T4 mRNA in brain is expressed by the rare invading T lymphocyte.

Discussion

The segregation of T4 and T8 with functionally distinct subsets of T cells suggests that these molecules may be important in the interaction of T lymphocytes with appropriate target cells. As a first step in understanding the specific role of these proteins, cDNA clones were obtained of both the T4 and TB molecules and their nucleotide sequences were determined (20, 70). Comparison of the deduced protein sequences of T4 and T8 indicates that these molecules share significant sequence and structural homology with immunoglobulin variable (V) domains and as members of the immunoglobulin supergene family. However, the N-terminal V-like domains of T4 and T8 are quite different: they share only 28% homology and are therefore less homologous to each other than each is to immunoglobulin light chains (FIG. 9A). Moreover, the regions of maximum conservation between T4 and T8 are also the regions of strongest homology to immunoglobulin and T cell receptor V regions. Thus, the immunoglobulin-like domains of these two molecules, although structurally similar, show significant sequence divergence consistent with the hypothesis that they recognize different molecules on different subsets of target cells.

The V-like region structural homology shared by the N-terminal domains of T4 and T8 may be of particular relevance to the functions of these proteins. Virtually all members of the immunoglobulin supergene family participate in the immune response (62). Moreover, the individual members of this family show a strong tendency to associate with each other to form dimers. This association is apparent in the interaction of the heavy and light chains of immunoglobulin, the alpha and beta chains of the T cell antigen receptor, $\beta_2$-micro-globulin and class I MHC proteins and the alpha and beta chains of class II MHC molecules. The T8 glycoprotein forms a disulphide bond with T6, a presumed MHC-like molecule, on the surface of thymocytes (82), and exists as multimers of the 32 kd subunit on peripheral T lymphocytes (83). The presence of four V-like domains in T4 indicates that these regions associate with one another as well as with specific ligands on the surface of other cells or viruses. These specific affinities of immunoglobulin-like molecules may be essential for the recognition functions of T4 and T8.

Evolution of T4

In the immunoglobulin and T cell antigen receptor genes, the V and J exons are widely separated and become juxtaposed only after a somatic recombination event (62, 63). The T4 mRNA encodes four contiguous V- and J-like elements without the requirement for DNA recombination events. It is therefore possible that T4 reflects a more primitive gene that evolved before the emergence of rearrangement mechanisms. Further support for this derives from recent observations that the first V-like region of T4 (V1) is split by an intron not present in the V genes encoding either the immunoglobulins or T cell antigen receptors. Accumulating evidence suggests that it is far more likely for introns to be precisely removed during evolution that for introns to be inserted in a previously intron-free environment. Thus, T4 may represent an ancestral immunoglobulin gene which underwent duplications, divergence, and rearrangement to generate the current immunoglobulin gene family. Although functional in a far more complex immune system at present, T4 may reflect receptors operative in more primitive cellular immune responses. Primitive immune responses, such as those of invertebrates, do not appear to involve a diverse repertoire of receptor molecules, but in the simplest cases are restricted to a distinction between self and nonself (85, 86) and are likely to be accommodated by a "static" set of genes that do not undergo rearrangement.

Whatever the order of appearance of T4 in evolutionary time, the organization of this gene reveals an interesting example of exon shuffling. T4 consists of four V-J-like domains, a J-like region and a transmembrane segment, each snaring homology with different members of the immunoglobulin supergene family. The V- and J-like domains are homologous to the equivalent regions of both immunoglobulins and the T cell antigen receptor chains; the transmembrane domain shows considerable homology to this region in the β-chains of class II MHC molecules (FIG. 9C). T4, therefore, consists of a collection of exons conserved in several members of the immunoglobulin supergene ramily which are shuffled in difterent ways to generate a large number of different molecules which participate in the immune response.

T4 is the AIDS Virus Receptor

The data provided herein suggest a mechanism of AIDS virus infection which initially involves the specitic association of the AIDS virus with T4 molecules on the cell surface. This association may be demonstrated on T lymphocytes, B lymphocytes, and epithelial cells, and therefore does not require the participation of additional T cell-specific proteins. Additionally, the data provided herein indicates that the T4-AIDS virus complex is internalized via receptor-mediated endocytosis and the viral envelope then fuses with the limiting membrane of the endosome, releasing the nucleocapsid into the cytoplasm. Viral replication and transcription can then occur in both lymphoid and non-lymphoid cell lines. Moreover, the T4 gene is expressed in the brain as well as in lymphocytes, providing an explanation for the dual neurotropic and lymphotropic character of the AIDS virus. In this manner, a T lymphocyte surface protein important in mediating effector cell-target cell interations has been exploited by a human retrovirus to specifically target the AIDS virus to populations of $T4^+$ cells.

Cell surface receptors have been identified for a number of enveloped viruses and the pattern of expression of these receptors is often responsible for the host range and tropic properties of specific viruses (74, 76). Some viruses will infect only a narrow range of cell types, reflecting the expression of the viral receptor on specific populations of target cells. Rabies virus, for example, interacts with the nicotinic acetylcholine receptor (87) and infects largely skeletal muscle and neurons, whereas the Epstein-Barr virus interacts with the C3d complement receptor type 2 (88) and intects B lymphocytes. Other viruses, such as the myxoviruses, interact with ubiquitously distributed sialic acid residues on the cell surface and infect a much broader range of cell types.

The restricted expression of cell surface receptors provides only one explanation for viral tropism. Some viruses will replicate only in a restricted set of differentiated cell types whereas others will only be efficiently transcribed in specific cell types. Hence, the Moloney murine leukemia virus (Mo-MuLV) induces T cell lymphomas in newborn mice, yet the closely-related Friend helper murine leukemia virus (Fr-MuLV) induces primarily erythroleukemias (89, 90, 91). This tropism is thought to result from differences in the LTRs which facilitate the efficient transcription of the Mo-MuLV genome in T lymphocytes and the Fr-MuLV genome in erythroid precursors (92, 93, 94).

As indicated herein, the primary tropic determinant of the AIDS virus is the expression of the T4 protein on the surface of the target cell. In vivo infection is restricted to lymphoid cells and myeloid cells as well as brain cells: three populations which express T4. In vitro demonstrations indicate that the introduction of T4 into $T4^-$ human B lymphocytes and epithelial cells, cells which are not natural targets for AIDS virus, renders these cells susceptible to productive infection by AIDS virus.

EXAMPLE 1

Soluble T4 Fragments

Soluble T4 glycoprotein fragments may be prepared using limited protease digestion from cell preparations. Alternatively, a DNA construct encoding a portion of T4 and lacking the transmembrane domain, a region containing neutral and hydrophobic residues, may be engineered. Such a fragment would be soluble in an aqueous solution and would contain a leader (signal) sequence. Therefore, in a mammalian cell, the modified protein may be directed to the rough endoplasmic reticulum/golgi complex and eventually secreted from the cell.

EXAMPLE 2

Treatment of AIDS Patients

Soluble T4 glycoprotein fragments may be administered to a subject infected with a human immunodeficiency virus, either alone or complexed with a pharmaceutically acceptable carrier, so as to bind AIDS viruses in the blood and body fluids, or to block AIDS virus infection of $T4^+$ cells in vivo.

Additionally, a patients' blood may be cycled through a chromatography column containing either immobilized T4 glycoproteins or soluble T4 fragments so that the AIDS virus may be separated from the blood. Such measures may affort the immune system the capacity to recover and mount a more effective immunologic response against the AIDS virus, i.e. allow uninfected T4+ T cells to proliferate.

EXAMPLE 3

Production of Soluble T4 Fragments

A cDNA encoding the membrane-bound T4 protein (pT4B) has been isolated, characterized, and expressed in a variety of mammalian cell types (70). Soluble T4 fragments may be produced in bacterial, yeast, insect, and mammalian systems. Because the T4 protein is likely to fold in a complex manner and be glycosylated, expression in a mammalian system may be preferable. A soluble T4 fragment may be produced by truncating pT4B after the $V_4J_4$ domain. The resulting DNA fragment would terminate before the transmembrane segment, which begins at approximately nucleotide position 1264 (FIG. 6). This. recombinant DNA molecule would therefore lack both the transmembrane and the cytoplasmic domains. The EcoRI-HpaII fragment, which encompasses nucleotides 1 through 1252, may be isolated by assemblying it from smaller fragments of pT4B. Alternatively, the membrane-spanning segment alone may be deleted, leaving the $V_4J_4$ domain fused to the cytoplasmic domain. One approach would be to delete the fragment spanning the HpaII sites from nucleotides 1252–1342 from pT4B. Such constructs would maintain the T4 signal sequence necessary for entry into the rough endoplasmic reticulum/golgi complex and eventual secretion from the cell. In addition, these constructs would maintain the extracellular portion of the T4 protein in which the binding domain for the human immunodeficiency virus envelope glycoprotein exists.

In order to express soluble T4 fragments in mammalian systems, the modified T4 cDNA fragment would be subcloned into vectors containing strong eukaryotic promoters/enhancers as well as polyadenylation sites required for cleavage and polyadenylation of the RNA. For example, the simian virus (SV40) early promoter and enhancer may be positioned upstream from the soluble T4 cDNA fragment. Transcription termination and RNA polyadenylation would be achieved by placing the polyadenylation site of either SV40 or the human growth hormone gene, downstream from the soluble T4 cDNA fragment. Introduction of a construct containing these elements together with a selectable marker into eukaryotic cells by any of several methods known in the art would lead to the stable integration of exogenous DNA. Transf ormants selected by virtue of their ability to grow in selective media would secrete soluble T4 fragments into the culture supernatant. Soluble T4 fragments may be detected in the supernatant by one of several assays, e.g. radioimmunoprecipitation, and then purified.

Purification and characterization of soluble T4 fragments may be greatly enhanced by constructing a cell line which overexpresses the secreted protein. Strategies which allow the overexpression of proteins have been employed in bacteria, yeast, insect, and mammalian systems. Inducible expression systems have also been employed in bacteria and yeast to overproduce proteins which may be toxic if constitutively expressed. Overexpression of soluble T4 fragments may be accomplished by amplifying the soluble T4 expression construct, resulting in constitutive overexpression. The amplification of dihydrofolate reductase (dhfr) genes by growth in progressively increased concentrations of the drug methotrexate, an antagonist of dhfr, has been widely employed. Since the amplified unit is not limited to dhfr coding sequences, this approach results in the coamplification of sequences adjacent to them. Therefore, dhfr may be used as a selectable marker and as a means of coamplifying newly introduced sequences. This strategy has been successfully employed to increase the expression of several different genes cotransformed with dhfr plasmids. An alternative amplification scheme involves cotranstection ot the soluble T4 cDNA expression construct with the plasmid pdLAT-3 followed by a selection scneme as previously described (102).

Therefore, the soluble T4 cDNA expression construct may be cotranstected with a dhfr expression plasmid. Alternatively, the dhfr gene can reside on the same plasmid as the soluble T4 cDNA fragment, allowing linked cotransformatilon. Transtection of these constructs into dhfr-deficient ($dhfr^-$) Chinese hamster ovary (CHO) cells and subsequent selection in methotrexate would permit the isolation of stable transformants that express newly introduced sequences. Several clones may be purified and culture supernatants may be collected and assayed for the presence of soluble T4 fragments. Clones which produce the greatest levels of soluble T4 fragments may be further characterized by Northern and Southern blot analyses. These cell lines may then be cultivated in selective media containing stepwise increased concentrations of methotrexate. This selective pressure results in the amplification of the newly introduced dhfr gene and adjacent T4 sequences. After reaching the highest methotrexate concentration, surviving cells may be subjected to Northern and Southern blot analyses to determine the extent of amplification and culture supernatants may be examined for the presence of soluble T4 fragments.

In order to characterize the soluble T4 fragments in the culture supernatant, several transformants may be metabolically labeled with ($^{35}S$)-methionine. Cell lysates and supernatants may then be analyzed by radioimmunoprecipitation and Western blot analysis using commercially available anti-T4 antibodies. SDS-polyacrylamide gel electrophoresis may be performed on the precipitates and a band of the predicted relative molecular mass ($M_r$) of the secreted, truncated form of T4 would be observed. Because it is synthesized in a mammalian system, this protein would be properly glycosylated and folded, i.e. disulphide bridges would be formed. In order to purify the soluble T4 fragments from culture supernatant, immunoaffinity column chromatography may be performed using anti-T4 antibodies. Protein bound to the column would be eluted at high salt concentrations and low pH. SDS-polyacrylamide gel electrophoresis of the eluted material would be performed in order to determine the $M_r$ and purity of the eluted protein fraction. In addition, radioimmunoprecipitation and Western blot analysis may also be performed in order to further characterize the affinity-purified material.

Similar approaches may be undertaken in bacteria, yeast and insects in order to produce a soluble T4 fragment. In addition, fragments smaller in size than the one described herein, e.g. containing the $V_1J_1$ domain only, may also be produced in all expressions systems.

EXAMPLE 4

Preparation of Anti-Soluble T4 Fragment Antibodies

Eight week old Balb/c mice may be injected intraperitoneally with 50 micrograms of a purified soluble T4 fragment of the present invention (prepared as described above) in complete Freund's adjuvant, 1:1 by volume. Mice may then be boosted, at monthly intervals, with the soluble T4 fragment mixed with incomplete Freund's adjuvant, and bled through the tail vein. Immunoglobulin cuts of sera may be generated by ammonium sulfate precipitation and specific anti-soluble T4 tragment antibodies may be purfified by affinity chromatography using an immobilized T4 fragment.

EXAMPLE 5

Preparation of Soluble T4 Fragment Anti-Idiotypic Antibodies

Syngenic and congenic mice may be injected intraperitoneally with 50 micrograms of a purified anti-soluble T4 fragment antibody, of the present invention (prepared as described above) in complete Freund's adjuvant and boosted with the anti-soluble T4 fragment antibody in incomplete Freund's adjuvant monthly. On days 4, 3, and 2 prior to fusion, mice may be boosted intravenously with 50 micrograms of immunoglobulin in saline. Splenocytes may then be fused with P3X63 AG8.653 non-secreting myeloma cells according to procedures which have been described and are known in the art to which this invention pertains. Two weeks later, hybridoma supernatants may be screened for binding activity against anti-soluble T4 fragment antibodies by radioimmunoassay. Positive clones may then be assayed for the ability to bind a human immunodeficiency virus envelope glycoprotein and AIDS virus. Alternatively, using the "one-step" procedure, mice may be injected intraperitoneally with a soluble T4 fragment in complete Freund's adjuvant, boosted intravenously with the soluble T4 fragment in saline, and mice spleen cells fused with myelomas as above. Hybridoma supernatants may then be assayed directly for soluble T4 tragment anti-idiotypic antibodies.

References

1. E. L. Reinherz et al., "Discrete Stages of Human Intrathymic Differentiation: Analysis of Normal Thymocyte and Leukemic Lymphoblasts of T Cell Lineage", Proc. Natl. Acad. Sci. USA 77: 1588–1592 (1980).
2. E. L. Reinherz and S. F. Schlossman, "The Differentiation and Function of Human T Lymphocytes", Cell 19: 821–827 (1980).
3. M. L. Blue et al., "Coexpression of T4 and T8 on Peripheral Blood T Cells Demonstrated by Two-color Fluoroescence Flow Cytometry", J. Immunol. 134: 2281–2286 (1985)
4. E. G. Engleman et al., "Activation of Human T Lymphocyte subsets: Helper and Suppressor/Cytotoxic T Cells Recognize and Respond to Distinct Histocompatibility Antigens", J. Immunol. 127: 2124–2129 (1981)
5. A. M. Krensky et al., "Long-term Human Cytolytic T-cell Lines Allospecific for HLA-DR6 Antigen Are OKT4$^+$ ", Proc. Natl. Acad. Sci. USA 79: 2365–2369 (1982).
6. S. C. Meuer, S. F. Schlossman and E. Reinherz, "Clonal Analysis of Human Cytotoxic T Lymphocytes T4$^+$ and T8$^+$ Effector T Cells Recognize Products of Different Major Histocompatibility Complex Regions", Proc. Natl. Acad. Sci. USA 79: 4395–4399 (1982).
7. W. E. Biddison et al., "Possible Involvement of the OKT4 Molecule in T Cell Recognition of Class II HLA Antigens", J. Exp. Med. 156: 1065–1076 (1982) .
8. D. R. Wilde et al., "Evidence Implicating L3T4 in Class II MHC Antigen Reactivity Monoclonal Antibody GK 15 (Anti-L3T4) Blocks Class II MHC Antigen-Specific Proliferation, Release of Lymphokines and Binding by Cloned Murine Helper T Lymphocyte Lines", J. Immunol. 131: 2178–2183 (1983).
9. S. L. Swain, "T Cell Subsets and the Recognition of MHC Class", Immunol. Rev. 74: 129–142 (1983).
10. Y. Thomas et al., "Functional Analysis of Human T Cell Subsets Defined by Monoclonal Antibodies. IV. Induction of Suppressor Cells Within the OKT4$^+$ Population", J. Exp. Med. 154: 459–467 (1981).
11. E. G. Engleman et al., "Antibodies to Membrane Structures that Distinguish Suppressor/Cytotoxic and Helper T Lymphocyte Subpopulations Block the Mixed Leukocyte Reaction in Man", J. Exp. Med. 154: 193–198 (1981).
12. P. Marrack et al., "The Major Histocompatibility Complex-restricted Antigen Receptor on T Cells. II. Role of the L3T4 Product", J. Exp. Med. 158: 1077–1091 (1983).
13. L. Rogozinski et al., "The T4 Surface Antigen is Involved in the Induction of Helper Function", J. Immunol. 132: 735–739 (1984).
14. S. L. Swain, "Significance of Lyt Phenotypes: Lyt2 Antibodies Block Activities of T Cells that Recognize Class I Major Histocompatibility Complex Antigens Regardless of Their Function", Proc. Natl. Acad. Sci. USA 78: 7101–7105 (1981).
15. U. Landegren et al., "Selective Inhibition of Human T Cell Cytotoxicity at Levels of Target Recognition of Initiation of Lysis by Monoclonal OKT3 and Leu-2a Antibodies", J. Exp. Med. 155: 1579–1584 (1982).
16. R. M. Zinkernagel and P. C. Doherty, "MHC-restricted Cytotoxic T Cells: Studies on the Biological Role of Polymorphic Major Transplantation Antigens Determining T Cell Restriction, Specificity, Function, and Responsiveness", Adv. Immunol. 27: 52–177 (1979).
17. J. Kappler et al., "The Major Histocompatibility Complex-Restricted Antigen Receptor on T Cells in Mouse and Man: Identification of Constant and Variable Peptides", Cell 35: 295–302 (1983).
18. O. Acuto et al., "The Human T Cell Receptor: Appearance in Ontogeny and Biochemical Relationship of Alpha and Beta Subunits on IL-2 Dependent Clones and T Cell Tumors", Cell 34: 717–726 (1983).
19. P. Kavathas et al., "Isolation of the Gene Coding for the Human T Lymphocyte Antigen Leu-2 (T8) by Gene Transfer and cDNA Subtraction", Proc. Natl. Acad. Sci. USA 81: 7688–7692 (1984).
20. D. R. Littman et al., "The Isolation and Sequence of the Gene Encoding T8: A Molecule Defining Functional Classes of T Lymphocytes", Cell 40: 237–246 (1985).
21. V. P. Sukhatma et al., "The T Cell Differentiation Antigen Leu-2/T8 is Homologous to Immunoglobulin and T Cell Receptor Variable Regions", Cell 40: 591–597 (1985).
22. S. M. Friedman et al., "OT-CLL: A Human T Cell Chronic Lymphocytic Leukemia That Produces IL-2 in High Titer", J. Immunol. 128: 935–940 (1982).
23. D. A. Thurley-Lawon, L. Chess and J. L. Strominger, "Suppression of In Vitro Epstein-Barr Infection: A New Role for Adult Human T Cells", J. Exp. Med. 146: 495–508 (1977).
24. J. W. Goding, "The Chromic Chloride Method of Coupling Antigens to Erythrocytes: Definition of Some Important Parameters", J. Immunol. Methods 10: 61–66 (1976).
25. F. L. Graham and A. J. van der Eb, "A New Technique for the Assay of Infectivity of Human Adenovirus DNA", Virology 52: 456–467 (1973).
26. M. Wigler et al., "Biochemical Transfer of Single-Copy Eucaryotic Genes Using Total Cellular DNA as Donor", Cell 14: 725–731 (1978).
27. M. Wigler et al., "Transfer of Purified Herpes Virus Thymidine Kinase Gene to Cultured Mouse Cells", Cell 11: 223–232 (1977).

28. J. M. Chirgwin et al., "Isolation of Biologically Active Ribonucleic Acid fron Sources Enriched in Ribonuclease", Biochemistry 18: 5294–5299 (1979).

29. H. Aviv and P. Leder, "Purification of Biologically Active Globin Messenger RNA by Chromatography on Oligothymidylic Acid-Cellulose", Proc. Natl. Acad. Sci. USA 69: 1408–1412 (1972).

30. T. Huynh, R. A. Young and R. W. Davis, "Construction and Screening cDNA Libraries in gt10 and gt11", *DNA Cloning Techniques—A Practical Approach*, D. M. Glover, ed. (Oxford: IRL Press), in press.

31. T. Maniatis et al., "The Isolation of Structural Genes from Libraries of Eucaryotic DNA", Cell 15: 687–701 (1978).

32. M. M. Davis et al., "Cell-Type-Specific cDNA Probes and the Murine I Region: the Localization and Orientation of $A^d$ Alpha", Proc. Natl. Acad. Sci. USA 81: 2194–2198 (1984).

33. T. Maniatis, E. F. Fritch and J. Sambrook, *Molecular Cloning* (Cold Spring Harbor, N.Y.; Cold Spring Harbor Laboratory) (1982).

34. P. W. J. Rigby et al., "Labeling Deoxyribonucleic Acid to High Specific Activity In Vitro by Nick Translation with DNA Polymerase I", J. Mol. Biol. 113: 237–251 (1977).

35. J. Vieira and J. Messing, "The pUC Plasmids, an M13mp7-Derived System for Insertion Mutagenesis and Sequencing with Synthetic Universal Primers", Gene 19: 259–268 (1982).

36. F. Sanger, S. Nicklen and A. Coulson, "DNA Sequencing with Chain-Terminating Inhibitors", Proc. Natl. Acad. Sci. USA 74: 5463–5467 (1977).

37. E. Southern, "Detection of Specific Sequences Among DNA Fragments Separated by Gel Electrophoroesis", J. Mol. Biol. 98: 503–517 (1975).

38. G. M. Church and W. Gilbert, "Genomic Sequencing", Proc. Natl. Acad. Sci. USA 81: 1991–1995 (1984).

39. R. H. Scheller et al., "A Family of Genes that Codes for ELH, a Neuropeptide Eliciting a Stereotyped Pattern of Behavior in Aplysia", Cell 28: 707–719 (1982).

40. K. Zinn, D. DiMaio and T. Maniatis, "Identification of Two Distinct Regulatory Regions Adjacent to the Human Beta-Interferon Gene", Cell 34: 865–879 (1983).

41. C. Terhorst et al., "Further Structural Studies of the Heavy Chain of HLA Antigens and Its Similarity to Immunoglobulins", Proc. Natl. Acad. Sci. USA 74: 4002–4006 (1977).

42. J. A. Hedo, L. C. Harrison and J. Roth, "Binding of Insulin Receptors to Lectins: Evidence for Common Carbohydrate Determinants on Several Membrane Receptors", Biochemistry 20: 3385–3393 (1981).

43. U. K. Laemmli, "Cleavage of Structural Proteins During the Assembly of the Head of Bacteriophage T4", Nature 227: 680–685 (1970).

44. R. Mann, R. C. Mulligan, and D. Baltimore, Construction of a retrovirus packaging mutant and its use to produce helper-free defective retrovirus, Cell 33, 153–159 (1983).

45. F. Barre-Sinoussi,et al., Isolation of a T lymphotropic retrovirus from a patient at risk for acquired immune deficiecny syndrome (AIDS), Science 220, 868–871 (1983).

46. J. S. McDougal, et al., Cellular tropism of the human retrovirus HTLV-III/LAV. I. Role of T cell activation and expression of the T4 antigen, J. Immol. 135, 3151–3162 (1985).

47. J. S. McDougal, et al., Immunoassay for the detection and quantitation of infectious human retrovirus, lymphadenopathy-assoicated virus (LAV) , J. Immunol. Meth. 76, 171–183 (1985).

48. J. S. McDougal, et al., Binding of HTLV-III/LAV to $T4^+$ T cells by a complex of the 110K viral protein and the T4 molecule, Science 231, 382–385 (1986).

49. C. B. Reimer, et al., Standardization of ligand binding assays for alpha-fetoprotein. In Immunofluorescence and Related Staining Techniques. W., Knapp, K. Holubar, and G. Wick, eds. (Amsterdam:Elsevier/North Holland Press) p. 189 (1978).

50. M. B. Wilson and P. K. Nakane, Recent developments in the periodate method of conjugating horseradish peroxidase (HRPO) to antibodies. In Immunofluorescence and Relating Staining Techniques, W. Knapp, K. Holubar, and G. Wick, eds. (Amsterdam: Elsevier/North Holland Press), p. 215 (1978) .

51. J. Porath, R. Axen, and S. Ermback, Chemical coupling of proteins to agar, Nature 215, 1491–1493 (1967).

52. B. J. Poiesz, et al., Detection and isolation of type C retrovirus particles from fresh and cultured lymphocytes of a patient with cutaneous T cell lymphoma. Proc; Natl. Acd. Aci. USA 77, 7415–7419 (1980).

53. P. Clapham, K. Nagy, and R. A. Weiss, Pseudotypes of human T-cell virus types 1 and 2: Neutralization by pateints' sera, Proc. Natl. Acad. Sci. USA 81, 2886–2889 (1984).

54. A. G. Dalgleish, et al., The CD4 (T4) antigen is an essential component of the receptor for the AIDS retrovirus, Nature 312, 763–766 (1984).

55. M. Popovic, et al., Detection, isolation, and continuous production of cytopathic retorviruses (HTLV-III) from patients with AIDS and Pre-AIDS, Science 224, 497–500 (1984).

56. K. Nagy, et al., Human T-cell leukemia virus type 1: induction of sycytia and inhibition by patients' sera, Int. J. Cancer 32, 321–328 (1983).

57. D. M. Neville and H. Glossman, Molecular weight determination of membrane protein and glycoprotein subunits by discontinuous gel electrophoresis in dodecyl sulfate, Methods Enzymol. 32, 92–102 (1974).

58. A. Helenius, et al., On the entry of Semliki Forest virus into BHK-21 cells, J. Cell. Biol. 84, 404–420 (1980).

59. R. D. Cone and R. C. Mulligan, High-efficiency gene transfer into mammalian cells: Generation of helper-free recombinant retroviruses with broad mammalian host range, Proc. Natl. Acad. Sci. USA 81, 6349–6353 (1984).

60. F. W. Alt et al., "Probes for Specific mRNAs by Subtractive Hybridization: Anomalous Expression of Immunoglobulin Genes", in *Eucaryotic Gene Regulation*, R. Axel, T. Maniatis and C. F. Fox, eds. (New York: Academic Press), pp. 407–419 (1979) .

61. M. Kozak, "Comparison of Initiation of Protein Synthesis in Procaryotes, Eucaryotes and Organelles", Microbiol. Rev. 47: 1–45 (1983).

62. L. Hood, M. Kronenberg and T. Hunkapiller, "T Cell Antigen Receptors and the Immunoglobulin Supergene Family", Cell 40: 225–229 (1985).

63. S. Tonegawa, "Somatic Generation of Antibody Diversity", Nature 302: 575–581 (1983).

64. J. Kyte and R. F. Doolittle, "A Simple Method for Displaying the Hydropathic Character of a Protein", J. Mol. Biol. 157: 105–132 (1982).

65. G. von Heijne, "Patterns of Amino Acids Near Signal-Sequence Cleavage Sites", Eur. J. Biochem. 133: 17–21 (1983).

66. E. A. Kabat et al., "Sequences of Proteins of Immunological Interest" (Washington, D.C.; U.S. Department of Health and Human Services), p. 281 (1983) .

67. A. F. Williams et al., "Cell Surface Glycoproteins and the Origins of Immunity", In the Proceedings of the Sigrid Juselius Symposium, L. C. Andersson, C. G. Gahmberg and P. Ekblam, eds. (New York: Academic Press), in press (1984).

68. L. M. Amzel and R. J. Poljak, "Three-Dimensional Structure of Immunoglobulins", Ann. Rev. Biochem. 48: 961–997 (1979).

69. P. Y. Chou and G. D. Fasman, "Empirical Predictions of Protein Conformation", Ann. Rev. Biochem. 47: 251–276 (1978).

70. P. J. Maddon, et al., The isolation and nucleotide sequence of a cDNA encoding the T cell surface protein T4: A new member of the immunoglobulin gene family, Cell 42, 93–104 (1985).

71. R. A. Adams, A. Flowers and B. J. Davis, Direct implantation and serial transplatation of human acute lymphoblastic leukemia in hamsters, SB-2, Can. Res. 28, 1121–1125 (1968).

72. G. O. Gey, W. D. Coffman and M. T. Kubicek, Tissue culture studies of the proliferative capacity of cervical carcinoma and normal epithelium, Cancer Res. 12, 264–265 (1952).

73. R. J. V. Pulvertaft, Cytology of Burkitt's tumor (African lymphoma), Lancet I, 238–240 (1964).

74. N. J. Dimmock, Initial stages of infection with animal viruses, J. Gen. Virol. 59, 1–22 (1982).

75. J. White, M. Kielian and A. Helenius, Membrane fusion proteins of enveloped animal viruses, Quart. Rev. Biophys. 16, 151–195 (1983).

76. M. Marsh, The entry of enveloped viruses into cells by endocytosis, Biochem. J. 218, 1–10 (1984).

77. M. Kielian and A. Helenius, Entry of alphaviruses. In the Togaviridae and Flaviviridae, S. Schlesinger and M. J. Schlesinger, eds., (Plenum Publishing Corp.), pp. 91–119 (1986).

78. S. Ohkuma, and B. Poole, Fluorescence probe measurements of the intralysosomal pH in living cells and the pertubation of pH by various agents, Proc. Natl. Acad. Sci. USA 75, 3327–3331 (1978).

79. F. R. Maxfield, Weak bases and ionophore rapidly and reversibly raise the pH of endocytic vesicles in cultured mouse fibroblasts, J. Cell. Biol. 95, 676–681 (1982).

80. A. Helenius, M. Marsh, and J. White, Inhibition of Semliki Forest virus penetration by lysosomotropic weak bases, J. Gen. Virol. 59, 47–61 (1982).

81. R. T. Johnson and J. C. McArthur, AIDS and the brain, TINS 9, 91–94 (1986).

82. P. M. Snow, M. Van de Rijn and C. Terhorst, "Association Between the Human Thymic Differentiation Antigens T6 and T8", Eur. J. Immunol., in press (1985).

83. P. M. Snow and C. Terhorst, "The T8 Antigen is a Multimeric Complex of Two Distinct Subunits on Human Thymocytes but Consists of Homomultimeric Forms on Peripheral Blood T Lymphocytes", J. Biol. Chem. 258: 14675–14681 (1983).

84. C. Terhorst et al., "Biochemical Analysis of Human T Lymphocyte Differentiation Antigens T4 and T5", Science 209: 520–521 (1980).

85. W. H. Hildemann, "Immunocompetance and Allogeneic Polymorphism Among Invertebrates", Transplantation 27: 1–3 (1979).

86. V. L. Scofield et al., "Protochordate Allorecognition is Controlled by a MHC-like Gene System", Nature 295: 499–502 (1982).

87. T. L. Lentz, et al., Is the acetylcholine receptor a rabies virus receptor ?, Science 215, 182–184 (1982).

88. J. D. Fingeroth, et al., Epstein-Barr virus receptor of human B lymphocytes is the C3d receptor CR2, Proc. Natl. Acad, Sci. USA 81, 4510–4514 (1984).

89. P. E. Tambourin, et al., The physiopathology of Friend leukemia, Leukemia Res. 3, 117–129 (1979).

90. A. Oliff, et al., Isolation of transplantable erythroleukemia cells from mice infected with helper-independent Friend murine leukemia virus, Blood 58, 244–254 (1981).

91. J. E. Silver and J. M. Fredrickson, Susceptibility to Friend helper virus leukemias in CXB recombinant inbred mice, J. Exp. Med. 158, 1693–1702 (1983).

92. P. A. Chatis, et al., Role for the 3' end of the genome in determining disease specificity of Friend and Moloney murine leukemia viruses, Proc. Natl. Acad. Sci, USA. 80, 4408–4411 (1983).

93. P. A. Chatis, et al., A 3' end fragment encompassing the transcriptional enhancers of nondefective Friend virus confers erthyroleukemogenicity on Moloney leukemia virus, J. Virol. 52, 248–254 (1984).

94. A. Bosze, H. J. Thiesen and P. Charnay, A transcriptional enhancer with specificity for erythroid cells is located in the long terminal repeat of the Friend murine leukemia virus, EMBO J. 5, 1615–1623 (1986).

95. A. N. Barclay, et al., Immunoglobulin-related structures associated with vertebrate cell surfaces, in press.

96. M. O. Dayhotf, W. C. Barker and L. T. Hunt, Establishing homologies in protein sequences. In Methods in Enzymology. Enzyme Sturcture Part I, C. H. W. Hirs and S. N. Timasheff, eds. (New York: Academic Press), pp. 524–545 (1983).

97. Y. Yanagi, et al., A human T cell-specific cDNA clone encodes a protein having extensive homology to immunoglobulin chains, Nature 308, 145–149 (1984).

98. G. K. Sim, et al., Primary structure of human T-cell receptor β-chain, Nature 312, 771–775 (1984).

99. H. Saito, et al., A third rearranged and expressed gene in a clone of cytotoxic T lymphocytes, Nature 312, 36–40 (1984).

100. H. Saito, et al., Complete primary structure of the $E_\beta$ chain and gene of the mouse major histocompatibility complex, Proc. Natl. Acad. USA 80, 5520–5524 (1983).

101. M. Isobe, et al., The gene encoding the T-cell surface protein T4 is located on human chromsome 12, Proc. Natl. Acad. Sci. USA, 83, 4399–4402 (1986).

102. J. M. Roberts and R. Axel, Gene Amplification and Gene Correction in Somatic Cells, Cell 29, 109–119 (1982).

What is claimed is:

1. An isolated cDNA encoding a soluble peptide consisting essentially of a soluble portion of a T4 glycoprotein that binds to a human immunodeficiency virus envelope glycoprotein containing amino acids, which cDNA encodes the amino acid sequence set forth in SEQ ID NO: 2 from at least the amino acid at position 1 to the amino acid at position 134.

2. An isolated cDNA encoding a polypeptide which consists essentially of the sequence of amino acids set forth in SEQ ID NO: 2 from the amino acid at position 1 to the amino acid at position 397.

3. A vector which comprises the cDNA of claim 1 or 2.

4. The vector of claim 3, wherein the vector is a plasmid.

5. A viral vector which comprises the cDNA of claim 1 or 2.

6. A host vector system for the production of a polypeptide, which host vector system comprises the vector of claim 3 in a suitable host.

7. A host vector system of claim 6, wherein the suitable host is a bacterial cell, a eucaryotic cell, a mammalian cell, a yeast cell or an insect cell.

8. A method for producing a soluble polypeptide, which method comprises growing the host vector system of claim 6 under conditions permitting production of the polypeptide and recovering the polypeptide.

9. The plasmid of claim 4, wherein the soluble portion of the T-4 glycoprotein has the sequence encoded by the plasmid PT4B (ATCC No 68389) [SEQ ID NO:2].

10. An isolated cDNA consisting of nucleotides, the nucleotide sequence of which is set forth in SEQ ID NO:1 from the nucleotide at position 145 to the nucleotide at position 477.

* * * * *

SEQUENCE LISTING

<160> NUMBER OF SEQ ID NOS: 15

<210> SEQ ID NO 1
<211> LENGTH: 1742
<212> TYPE: DNA
<213> ORGANISM: Human
<220> FEATURE:

<221> NAME/KEY: CDS
<222> LOCATION: (76)..(1449)

<400> SEQUENCE: 1

```
caagcccaga gccctgccat ttctgtgggc tcaggtccct actgctcagc cccttcctcc        60
ctcggcaagg ccaca atg aac cgg gga gtc cct ttt agg cac ttg ctt ctg       111
                 Met Asn Arg Gly Val Pro Phe Arg His Leu Leu Leu
                   1               5                  10 gtg ctg caa ctg gcg ctc ctc cca gca gcc act cag gga aag aaa gtg       159
Val Leu Gln Leu Ala Leu Leu Pro Ala Ala Thr Gln Gly Lys Lys Val
         15                  20                  25 gtg ctg ggc aaa aaa ggg gat aca gtg gaa ctg acc tgt aca gct tcc       207
Val Leu Gly Lys Lys Gly Asp Thr Val Glu Leu Thr Cys Thr Ala Ser
     30                  35                  40 cag aag aag agc ata caa ttc cac tgg aaa aac tcc aac cag ata aag       255
Gln Lys Lys Ser Ile Gln Phe His Trp Lys Asn Ser Asn Gln Ile Lys
 45                  50                  55                  60 att ctg gga aat cag ggc tcc ttc tta act aaa ggt cca tcc aag ctg       303
Ile Leu Gly Asn Gln Gly Ser Phe Leu Thr Lys Gly Pro Ser Lys Leu
                 65                  70                  75 aat gat cgc gct gac tca aga aga agc ctt tgg gac caa gga aac ttc       351
Asn Asp Arg Ala Asp Ser Arg Arg Ser Leu Trp Asp Gln Gly Asn Phe
             80                  85                  90 ccc ctg atc atc aag aat ctt aag ata gaa gac tca gat act tac atc       399
Pro Leu Ile Ile Lys Asn Leu Lys Ile Glu Asp Ser Asp Thr Tyr Ile
         95                 100                 105 tgt gaa gtg gag gac cag aag gag gag gtg caa ttg cta gtg ttc gga       447
Cys Glu Val Glu Asp Gln Lys Glu Glu Val Gln Leu Leu Val Phe Gly
    110                 115                 120 ttg act gcc aac tct gac acc cac ctg ctt cag ggg cag agc ctg acc       495
Leu Thr Ala Asn Ser Asp Thr His Leu Leu Gln Gly Gln Ser Leu Thr
125                 130                 135                 140 ctg acc ttg gag agc ccc cct ggt agt agc ccc tca gtg caa tgt agg       543
Leu Thr Leu Glu Ser Pro Pro Gly Ser Ser Pro Ser Val Gln Cys Arg
                145                 150                 155 agt cca agg ggt aaa aac ata cag ggg ggg aag acc ctc tcc gtg tct       591
Ser Pro Arg Gly Lys Asn Ile Gln Gly Gly Lys Thr Leu Ser Val Ser
            160                 165                 170 cag ctg gag ctc cag gat agt ggc acc tgg aca tgc act gtc ttg cag       639
Gln Leu Glu Leu Gln Asp Ser Gly Thr Trp Thr Cys Thr Val Leu Gln
        175                 180                 185 aac cag aag aag gtg gag ttc aaa ata gac atc gtg gtg cta gct ttc       687
Asn Gln Lys Lys Val Glu Phe Lys Ile Asp Ile Val Val Leu Ala Phe
    190                 195                 200 cag aag gcc tcc agc ata gtc tat aag aaa gag ggg gaa cag gtg gag       735
Gln Lys Ala Ser Ser Ile Val Tyr Lys Lys Glu Gly Glu Gln Val Glu
205                 210                 215                 220 ttc tcc ttc cca ctc gcc ttt aca gtt gaa aag ctg acg ggc agt ggc       783
Phe Ser Phe Pro Leu Ala Phe Thr Val Glu Lys Leu Thr Gly Ser Gly
                225                 230                 235 gag ctg tgg tgg cag gcg gag agg gct tcc tcc tcc aag tct tgg atc       831
Glu Leu Trp Trp Gln Ala Glu Arg Ala Ser Ser Ser Lys Ser Trp Ile
            240                 245                 250 acc ttt gac ctg aag aac aag gaa gtg tct gta aaa cgg gtt acc cag       879
Thr Phe Asp Leu Lys Asn Lys Glu Val Ser Val Lys Arg Val Thr Gln
        255                 260                 265 gac cct aag ctc cag atg ggc aag aag ctc ccg ctc cac ctc acc ctg       927
Asp Pro Lys Leu Gln Met Gly Lys Lys Leu Pro Leu His Leu Thr Leu
    270                 275                 280
```

-continued

```
ccc cag gcc ttg cct cag tat gct ggc tct gga aac ctc acc ctg gcc    975
Pro Gln Ala Leu Pro Gln Tyr Ala Gly Ser Gly Asn Leu Thr Leu Ala
285                 290                 295                 300 ctt gaa gcg aaa aca gga aag ttg cat cag gaa gtg aac ctg gtg gtg   1023
Leu Glu Ala Lys Thr Gly Lys Leu His Gln Glu Val Asn Leu Val Val
                305                 310                 315 atg aga gcc act cag ctc cag aaa aat ttg acc tgt gag gtg tgg gga   1071
Met Arg Ala Thr Gln Leu Gln Lys Asn Leu Thr Cys Glu Val Trp Gly
            320                 325                 330 ccc acc tcc cct aag ctg atg ctg agc ttg aaa ctg gag aac aag gag   1119
Pro Thr Ser Pro Lys Leu Met Leu Ser Leu Lys Leu Glu Asn Lys Glu
        335                 340                 345 gca aag gtc tcg aag cgg gag aag ccg gtg tgg gtg ctg aac cct gag   1167
Ala Lys Val Ser Lys Arg Glu Lys Pro Val Trp Val Leu Asn Pro Glu
    350                 355                 360 gcg ggg atg tgg cag tgt ctg ctg agt gac tcg gga cag gtc ctg ctg   1215
Ala Gly Met Trp Gln Cys Leu Leu Ser Asp Ser Gly Gln Val Leu Leu
365                 370                 375                 380 gaa tcc aac atc aag gtt ctg ccc aca tgg tcc acc ccg gtg cag cca   1263
Glu Ser Asn Ile Lys Val Leu Pro Thr Trp Ser Thr Pro Val Gln Pro
                385                 390                 395 atg gcc ctg att gtg ctg ggg ggc gtc gcc ggc ctc ctg ctt ttc att   1311
Met Ala Leu Ile Val Leu Gly Gly Val Ala Gly Leu Leu Leu Phe Ile
            400                 405                 410 ggg cta ggc atc ttc ttc tgt gtc agg tgc cgg cac cga agg cgc caa   1359
Gly Leu Gly Ile Phe Phe Cys Val Arg Cys Arg His Arg Arg Arg Gln
        415                 420                 425 gca gag cgg atg tct cag atc aag aga ctc ctc agt gag aag aag acc   1407
Ala Glu Arg Met Ser Gln Ile Lys Arg Leu Leu Ser Glu Lys Lys Thr
    430                 435                 440 tgc cag tgc cct cac cgg ttt cag aag aca tgt agc ccc att          1449
Cys Gln Cys Pro His Arg Phe Gln Lys Thr Cys Ser Pro Ile
445                 450                 455 tgaggcacga ggccaggcag atcccacttg cagcctcccc aggtgtctgc cccgcgtttc   1509
ctgcctgcgg accagatgaa tgtagcagat cccacgctct ggcctcctgt tcgtcctccc   1569
tacaatttgc cattgtttct cctgggttag gccccggctt cactggttga gtgttgctct   1629
ctagtttcca gaggcttaat cacaccgtcc tccacgccat ttccttttcc ttcaagccta   1689
gcccttctct cattatttct ctctgaccct ctccccactg ctcatttgga tcc          1742

<210> SEQ ID NO 2
<211> LENGTH: 458
<212> TYPE: PRT
<213> ORGANISM: Human

<400> SEQUENCE: 2

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95
```

-continued

```
Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
            115                 120                 125

Ser Asp Thr His Leu Leu Gln Gly Gln Ser Leu Thr Leu Thr Leu Glu
        130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Pro Val Trp Val Leu Asn Pro Glu Ala Gly Met Trp
        355                 360                 365

Gln Cys Leu Leu Ser Asp Ser Gly Gln Val Leu Leu Glu Ser Asn Ile
370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
                405                 410                 415

Phe Phe Cys Val Arg Cys Arg His Arg Arg Arg Gln Ala Glu Arg Met
            420                 425                 430

Ser Gln Ile Lys Arg Leu Leu Ser Glu Lys Lys Thr Cys Gln Cys Pro
        435                 440                 445

His Arg Phe Gln Lys Thr Cys Ser Pro Ile
    450                 455

<210> SEQ ID NO 3
<211> LENGTH: 94
<212> TYPE: PRT
<213> ORGANISM: Human

<400> SEQUENCE: 3

Gln Gly Asn Lys Val Val Leu Gly Lys Lys Gly Asp Thr Val Glu Leu
 1               5                  10                  15
```

-continued

Thr Cys Thr Ala Ser Gln Lys Lys Ser Ile Gln Phe His Trp Lys Asn
                20                  25                  30

Ser Asn Gln Ile Lys Ile Leu Gly Asn Gln Gly Ser Phe Leu Thr Lys
            35                  40                  45

Gly Pro Ser Lys Leu Asn Asp Arg Ala Asp Ser Arg Arg Ser Leu Trp
 50                  55                  60

Asp Gln Gly Asn Phe Pro Leu Ile Ile Lys Asn Leu Lys Ile Glu Asp
 65                  70                  75                  80

Ser Asp Thr Tyr Ile Cys Glu Val Glu Asp Gln Lys Glu Glu
                85                  90

<210> SEQ ID NO 4
<211> LENGTH: 96
<212> TYPE: PRT
<213> ORGANISM: Mouse or Murine

<400> SEQUENCE: 4

Asp Val Gln Met Ile Gln Ser Pro Ser Ser Leu Ser Ala Ser Leu Gly
 1               5                  10                  15

Asp Ile Val Thr Met Thr Cys Gln Ala Ser Gln Gly Thr Ser Ile Asn
                20                  25                  30

Leu Asn Trp Phe Gln Gln Lys Pro Gly Lys Ala Pro Lys Leu Leu Ile
            35                  40                  45

Tyr Gly Ala Ser Ile Leu Glu Asp Gly Val Pro Ser Arg Phe Ser Gly
 50                  55                  60

Ser Arg Tyr Gly Thr Asp Phe Thr Leu Thr Ile Ser Ser Leu Glu Asp
 65                  70                  75                  80

Glu Asp Met Ala Thr Tyr Phe Cys Leu Gln His Ser Tyr Leu Pro Tyr
                85                  90                  95

<210> SEQ ID NO 5
<211> LENGTH: 14
<212> TYPE: PRT
<213> ORGANISM: Human

<400> SEQUENCE: 5

Thr Gly Cys Trp Ile Gly Arg Phe Gly Ser Leu Ile Tyr Cys
 1               5                  10

<210> SEQ ID NO 6
<211> LENGTH: 102
<212> TYPE: PRT
<213> ORGANISM: Human

<400> SEQUENCE: 6

Ser Gln Phe Arg Val Ser Pro Leu Asp Arg Thr Trp Asn Leu Gly Glu
 1               5                  10                  15

Thr Val Glu Leu Lys Cys Gln Val Leu Leu Ser Asn Pro Thr Ser Gly
                20                  25                  30

Cys Ser Trp Leu Phe Gln Pro Arg Gly Ala Ala Ala Ser Pro Thr Phe
            35                  40                  45

Leu Leu Tyr Leu Ser Gln Asn Lys Pro Lys Ala Ala Glu Gly Leu Asp
 50                  55                  60

Thr Gln Arg Phe Ser Gly Lys Arg Leu Gly Asp Thr Phe Val Leu Thr
 65                  70                  75                  80

-continued

Leu Ser Asp Phe Arg Arg Glu Asn Glu Gly Tyr Tyr Phe Cys Ser Ala
            85                  90                  95

Leu Ser Asn Ser Ile Met
            100

<210> SEQ ID NO 7
<211> LENGTH: 102
<212> TYPE: PRT
<213> ORGANISM: Human

<400> SEQUENCE: 7

Asp Ala Gly Val Ile Gln Ser Pro Arg His Glu Val Thr Glu Met Gly
 1               5                  10                  15

Gln Glu Val Thr Leu Arg Cys Lys Pro Ile Ser Gly His Asn Ser Leu
                20                  25                  30

Phe Trp Tyr Arg Gln Thr Met Met Arg Gly Leu Glu Leu Leu Ile Tyr
            35                  40                  45

Phe Asn Asn Asn Val Pro Ile Asp Asp Ser Gly Met Pro Glu Asp Arg
        50                  55                  60

Phe Ser Ala Lys Met Pro Asn Ala Ser Phe Ser Thr Leu Lys Ile Gln
 65                 70                  75                  80

Pro Ser Glu Pro Arg Asp Ser Ala Val Tyr Phe Cys Ala Ser Ser Phe
                85                  90                  95

Ser Thr Cys Ser Ala Asn
            100

<210> SEQ ID NO 8
<211> LENGTH: 99
<212> TYPE: PRT
<213> ORGANISM: Human

<400> SEQUENCE: 8

Gln Lys Val Thr Gln Ala Gln Thr Glu Ile Ser Val Val Glu Lys Glu
 1               5                  10                  15

Asp Val Thr Leu Asp Cys Val Tyr Glu Thr Arg Asp Thr Thr Tyr Tyr
                20                  25                  30

Leu Phe Trp Tyr Lys Gln Pro Pro Ser Gly Glu Leu Val Phe Leu Ile
            35                  40                  45

Arg Arg Asn Ser Phe Asp Glu Gln Asn Glu Ile Ser Gly Arg Tyr Ser
        50                  55                  60

Trp Asn Phe Gln Lys Ser Thr Ser Ser Phe Asn Phe Thr Ile Thr Ala
 65                 70                  75                  80

Ser Gln Val Val Asp Ser Ala Val Tyr Phe Cys Ala Leu Asp Ser Ser
                85                  90                  95

Ala Ser Lys

<210> SEQ ID NO 9
<211> LENGTH: 12
<212> TYPE: PRT
<213> ORGANISM: Human

<400> SEQUENCE: 9

Leu Val Phe Gly Leu Thr Ala Asn Ser Asp Thr His
 1               5                  10

<210> SEQ ID NO 10
<211> LENGTH: 12

```
<212> TYPE: PRT
<213> ORGANISM: Human
<400> SEQUENCE: 10

Leu Tyr Phe Gly Glu Gly Thr Arg Leu Thr Val Leu
 1               5                  10

<210> SEQ ID NO 11
<211> LENGTH: 13
<212> TYPE: PRT
<213> ORGANISM: Human

<400> SEQUENCE: 11

Trp Val Phe Gly Gly Gly Thr Lys Val Thr Val Leu Gly
 1               5                  10

<210> SEQ ID NO 12
<211> LENGTH: 12
<212> TYPE: PRT
<213> ORGANISM: Human

<400> SEQUENCE: 12

Thr Phe Gly Gly Gly Thr Lys Leu Glu Ile Lys Arg
 1               5                  10

<210> SEQ ID NO 13
<211> LENGTH: 12
<212> TYPE: PRT
<213> ORGANISM: Human

<400> SEQUENCE: 13

Ile Ile Phe Gly Ser Gly Thr Arg Leu Ser Ile Arg
 1               5                  10

<210> SEQ ID NO 14
<211> LENGTH: 31
<212> TYPE: PRT
<213> ORGANISM: Human

<400> SEQUENCE: 14

Ser Thr Pro Val Gln Pro Met Ala Leu Ile Val Leu Gly Gly Val Ala
 1               5                  10                  15
Gly Leu Leu Leu Phe Ile Gly Leu Gly Ile Phe Phe Cys Val Arg
            20                  25                  30

<210> SEQ ID NO 15
<211> LENGTH: 31
<212> TYPE: PRT
<213> ORGANISM: Human

<400> SEQUENCE: 15

Ser Thr Ser Ala Gln Asn Lys Met Leu Ser Gly Val Gly Gly Phe Val
 1               5                  10                  15
Leu Gly Leu Leu Phe Leu Gly Leu Gly Leu Phe Ile Tyr Phe Arg
            20                  25                  30
```